United States Patent [19]
Betbeder et al.

[11] Patent Number: 6,017,513
[45] Date of Patent: *Jan. 25, 2000

[54] MUCOSAL ADMINISTRATION OF SUBSTANCES TO MAMMALS

[75] Inventors: Didier Betbeder, Aucamville; Alain Etienne, Toulouse; Ignacio de Miguel, Plaisance du Touch; Roger Kravtzoff, Fourquevaux; Michel Major, Toulouse, all of France

[73] Assignee: Biovector Therapeutics, S.A., Labege Cedex, France

[ * ] Notice: This patent is subject to a terminal disclaimer.

[21] Appl. No.: 08/987,436

[22] Filed: Dec. 9, 1997

Related U.S. Application Data

[63] Continuation-in-part of application No. 08/774,920, Dec. 27, 1996.

[51] Int. Cl.[7] ............................ A61K 51/00; A61M 36/14
[52] U.S. Cl. ...................... 424/1.73; 424/1.11; 424/1.65; 424/1.53
[58] Field of Search ................................... 424/1.11, 1.53, 424/1.65, 1.69, 1.73, 9.1, 9.2, 184.1, 201.1, 204.1, 450, 9.3, 9.4, 9.5

[56] References Cited

U.S. PATENT DOCUMENTS

| | | |
|---|---|---|
| 4,148,876 | 4/1979 | Almeida et al. . |
| 4,196,191 | 4/1980 | Almeida et al. . |
| 4,900,556 | 2/1990 | Wheatley et al. . |
| 4,921,757 | 5/1990 | Wheatley et al. . |
| 5,151,264 | 9/1992 | Samain et al. . |
| 5,354,853 | 10/1994 | Staveski et al. . |

FOREIGN PATENT DOCUMENTS

| | | |
|---|---|---|
| 0 352 295 B2 | 1/1990 | European Pat. Off. . |
| 1564500 | 4/1980 | United Kingdom . |
| WO 94/20078 | 9/1954 | WIPO . |
| 9203162 | 3/1992 | WIPO . |
| WO 92/03162 | 3/1992 | WIPO . |
| 9420078 | 9/1994 | WIPO . |
| 9423701 | 10/1994 | WIPO . |
| WO 94/23701 | 10/1994 | WIPO . |
| 9606638 | 3/1996 | WIPO . |
| WO 96/06638 | 3/1996 | WIPO . |

OTHER PUBLICATIONS

Meisner, Dale, Chapter 3, "Liposomes as a Pulmonary Drug Delivery System" in Pharmaceutical Particulate Carriers—Therapeutic Applications, Edited by A. Rolland, Marcel Dekker (1993).
Almeida et al., Journal of Drug Targeting 3, 455–467 (1996).
Brownlie et al., Microbial Pathogenesis 14, 149–160 (1993).
Chidambaram et al., Drug Development and Industrial Pharmacy 21, 1009–1036 (1995).
Edman et al., Chapter 2, "Microspheres as a Nasal Drug Delivery System" in Pharmaceutical Particulate Carriers—Therapeutic Applications. Edited by A. Rolland. Marcel Dekker, Inc., 20–29 (1993).
El Guink et al., Vaccine 7, 147–151 (1989).
Illum et al., International Journal of Pharmaceutics 39, 189–199 (1987).
Larkin, Genetic Engineering News, 9 and 23 (Jul., 1996).
Meisner et al., Advanced Drug Delivery Reviews 16, 75–93 (1995).
Meisner, Dale, Chapter 3, "Microspheres as a Nasal Drug Delivery System" in Pharmaceutical Particulate Carriers—Therapeutic Applications. Edited by A. Rolland. Marcel Dekker, Inc. (1993).
Ray et al., The Journal of Infectious Diseases 167, 752–755 (1993).
Takeuchi et al., Chem. Pharm. Bull. 42, 1954–1956 (1994).
Thermes et al., Pharmaceutical Research 9, 1563–1567 (1992).

*Primary Examiner*—Jose' G. Dees
*Assistant Examiner*—Dameron Jones
*Attorney, Agent, or Firm*—Hoffmann & Baron, LLP; Irving N. Feit

[57] ABSTRACT

A novel method for the mucosal administration of a substance to a mammal is provided. The method comprises contacting a mucosal surface of the mammal with the substance in combination with a Biovector. The Biovector has a core that comprises a natural polymer, or a derivative or a hydrolysate of a natural polymer, or a mixture thereof. A preferred natural polymer is a polysaccharide or an oligosaccharide. The core is optionally coated with an amphiphilic compound, such as a lipid.

48 Claims, 11 Drawing Sheets

FIG-10

```
FLUORESCENCE INTENSITY (a.u.)
```

Top panel: y-axis 0 to 400
Bottom panel: y-axis 0 to 200
x-axis: n° FRACTION, 1 to 10

Legend:
- ─□─ INFLUENZA PROTEIN ALONE
- ─■─ SMBV FORMULATED INFUENZA PROTEIN
- ─♦─ PSC LABELLED FLUORESCEIN
- ─●─ LIPID MEMBRANE DPH LABELLED

MUCOSAL ADMINISTRATION OF SUBSTANCES TO MAMMALS

This application is a continuation-in-part of U.S. Ser. No. 08/774,920 filed on Dec. 27, 1996.

BACKGROUND OF THE INVENTION

A large number of pharmaceutical substances for various purposes have been developed for introduction into animals, including humans. The substances include therapeutic agents, such as drugs; prophylactic agents, such as antigens for use in vaccines; and diagnostic agents, such as labeled imaging agents. The substances may be introduced by a variety of enteral and parenteral modes of administration.

There has recently been a proliferation of potential and realized pharmaceutical compounds that are macromolecules, such as proteins and nucleic acid molecules. These macromolecular compounds present particular problems for drug delivery, since they tend to be unstable, poorly absorbed, and easily metabolized.

There has also been renewed interest in the mucosal administration of pharmaceutical substances. The mucosa refers to the epithelial tissue that lines the internal cavities of the body, such as the gastrointestinal tract, the respiratory tract, the lungs, and the genitalia. For the purpose of this specification, the mucosa will also include the external surface of the eye, i.e. the cornea.

Some common modes of mucosal administration include oral and nasal administrations. Currently known methods of ocular administration are subject to several limitations that compromise their effectiveness. These problems include rapid nasolacrimal drainage, poor corneal penetration, non-productive conjunctival loss, and unwanted systemic exposure.

Almeida et al. have reviewed the mucosal administration of vaccines in general, and nasal administration of vaccines in particular in the Journal of Drug Targeting 3, 456–467 1996). Mucosal immunity is based on the existence in the mucosa of mucosal-associated lymphoid tissue (MALT). These include gut-associated lymphoid tissue (GALT), bronchus-associated lymphoid tissue (BALT), and nasal-associated lymphoid tissue (NALT). Mucosal immunization is capable of inducing both a local (IgA) and systemic (IgG) immune response. In addition, there is a common mucosal immune system, whereby an antigen enters the MALT at a local site, and is transported through the regional lymph nodes to other mucosal surfaces, where an immune response is also induced.

Pharmaceutical substances may be administered either in the absence or in the presence of a carrier. Various purposes may be served by such carriers, such as the controlled release of biologically active molecules, and the targeting of biologically active molecules to specific tissues.

Illum et al. investigated three microspheres as potential nasal drug delivery systems. The microspheres were albumin, starch, and DEAE-Sephadex. Although these microspheres showed some promise, certain problems still need to be overcome.

For example, Illum et al. reported that the size of the microspheres must be greater than 10 μm. Such large particles, however, have certain disadvantages. For example, they cannot be sterilized by ultrafiltration, requiring other methods, such as the use of preservatives.

In addition, Illum et al. reported difficulty releasing drugs from microspheres having a cationic charge. There are advantages to positively charged microspheres, and the problems reported by Illum et al. must be overcome.

Liposomes are often used as carriers for substances. They have shown potential as controlled release drug delivery systems and as immunological adjuvants. The use of liposomes as carriers for vaccines is discussed in the article by Almeida et al. mentioned above. More specifically, the use of liposomes as carriers for influenza vaccines was discussed by El Guink et al., Vaccine 7, 147–151 (1989), and in U.S. Pat. No. 4,196,191 of the Burroughs Wellcome Company and International PCT Application WO 92/03162 of the Wellcome Foundation.

There are, however, disadvantages in the use of liposomes as carrier for active compounds. For example, only small amounts of one compound can generally be incorporated in a liposome, and the ratio of active compound to lipid is low. Moreover, the active compound is often released too early.

Liposomes also present certain manufacturing disadvantages. For example, detergents and solvents are used to increase solubility during one phase of the manufacturing process. These detergents and solvents must be eliminated from the drug at a later stage.

Other difficulties in using liposomes as drug delivery systems have been reported by Meisner in Chapter 3, page 31 of Pharmaceutical Particulate Carriers—Therapeutic Applications, A. Roland, ed., Marcel Dekker, 1993. There is, therefore, the need for a more flexible carrier for substances.

Other carriers for substances have been described in U.S. Pat. No. 4,921,757 and 4,900,556 of the Massachussets Institute of Technology; U.S. Pat. No. 5,354,853 of Genzyme Corporation; and European Patent 352 295 of Access Pharmaceuticals, Inc. For example, the Access patent describes a carrier for drugs and diagnostic agents having a multivalent binding agent, such as heparin. The multivalent binding agent is specific for endothelial surface determinants, and may be as large as three micrometers.

The carriers described in the Access patent have, however certain disadvantages. First, the Access carriers bind specifically to endothelial cells. Also, the Access patent describes only carriers pre-loaded with the drug or diagnostic agent prior to administration. Such methods can lead to instability. Thus, Examples X and XII on page 19 of the Access patent measure stability in hours. Also, the carriers described in the Access patent are generally too large to be subjected to microfiltration.

In addition to those mentioned above, numerous other microspheres and nanospheres are known. These include polyacrylate, latex, and polylactide polymers. Björk and Edman, International Journal of Pharmaceutics 47, 233 (1988) reported that starch, cellulose, and dextran microspheres can act as absorption enhancers if they satisfy certain criteria, i.e., they must be water absorptive, water insoluble, and administered in powder form to the nose.

A new type of improved carrier was described by Biovector Therapeutics, S.A. in International PCT Application WO 94/20078. These carriers, called Supramolecular Biovectors (SMBVs) act as solvated suspensions in water, while still maintaining their integrity as substance-encapsulating particles. These SMBVs comprise a non-liquid hydrophilic core, such as a cross-linked polysaccharide or a cross-linked oligosaccharide and, optionally, an external layer comprising an amphiphilic compound, such as a phospholipid. The Biovector optionally has cationic or anionic ligands grafted into the polysaccharide or oligosaccharide core. The Biovector also optionally contains a layer of lipid compounds grafted onto the core by covalent bonds. See International PCT Application WO 94/23701. These Biovectors have been described as being useful in vaccines, such as in CMV vaccines. See International PCT Application WO 96/06638.

There is a need for a carrier that is capable of delivering substances to animals, including humans, efficiently, and that avoids the disadvantages of prior art carriers. An object of the present invention is to provide a method for the administration of biologically active molecules and other substances to mammals in a way that avoids the disadvantages discussed above. More specifically, an object of the present invention is to provide a method for administering substances to mammals by means of a carrier that directs the substance to the mucosa in a non-specific manner, that is capable of being loaded with the substance immediately prior to administration, that is of a size susceptible to microfiltration, and that is stable for up to twelve months and even one or more years.

SUMMARY OF THE INVENTION

These and other objectives as will be appreciated by those having ordinary skill in the art have been met by providing a novel method for the mucosal administration of a substance to a mammal. The method comprises contacting a mucosal surface of the mammal with the substance in combination with a Biovector. The Biovector has a core that comprises a natural polymer, or a derivative or a hydrolysate of a natural polymer, or a mixture thereof.

The invention further relates to the use of Biovectors associated with one or more biologically active compounds to prepare a composition for therapeutic or preventative purposes, especially against infectious agents, via mucosal administration to a mammal.

BRIEF DESCRIPTION OF THE DRAWINGS

FIG. 8 shows normalized counts per minute/milliliter (cpm/ml) versus time for sublingually administered $^{111}In$-DPTA+SMBV and $^{111}In$-DPTA.

FIG. 9 is a bar graph comparing the plasmatic AUC (area under curve) for the following routes of administration: intravenous, nasal, vaginal and sublingual.

FIG. 10 shows sucrose gradient analysis (0 to 20%) of collected fractions for SMBV/influenza antigen formulation, the polysaccharide core (PSC) and the lipid membrane, analyzed by protein intrinsic fluorescence at 280 nm and the microBSA technique.

FIG. 11 shows sucrose gradient analysis (0 to 20%) of collected fractions for SMBV-Q2 with four different outer layer components (DPPC, DPPC/Cholesterol, egg-PC/Cholesterol and egg-PC) and HA alone, analyzed by protein intrinsic fluorescence at 280 nm and the microBSA technique.

DETAILED DESCRIPTION OF THE INVENTION

In the description of the invention below, the following interpretations will apply. The word "comprise" followed by an element of the invention used in describing an embodiment of the invention means that the embodiment includes, but is not necessarily limited to, that element. The embodiment may include other members of the same element or other elements as well. An element disclosed in the singular, i.e. "substance," does not preclude the presence of more than one element, i.e. "substances." All numbers are approximate, unless the language of the specification or its context indicates otherwise.

It has unexpectedly been discovered that Biovectors, as described in International PCT Application WO 94/23701, WO 94/20078, and WO 96/06638, are particularly well suited for the mucosal administration of substances to mammals, including farm animals, pet animals, laboratory animals, and humans. The mucosa refers to the epithelial tissue that lines the internal cavities of the body. For example, the mucosa comprises the alimentary canal, including the mouth, esophagus, stomach, intestines, and anus; the respiratory tract, including the nasal passages, trachea, bronchi, and lungs; and the genitalia. For the purpose of this specification, the mucosa will also include the external surface of the eye, i.e. the cornea.

The substance in combination with the Biovector may be added to any mucosal surface. Some particularly suitable mucosal surfaces include, for example, the nasal, buccal, oral, vaginal, ocular, auditory, pulmonary tract, urethral, digestive tract, or rectal surface.

The cross-linked polysaccharide or oligosaccharide preferably binds non-specifically to the mucosal surface. Applicants have unexpectedly discovered that non-specifically binding polysaccharides and oligosaccharides in accordance with the invention make superior carriers for delivering substances to mucosal surfaces. This discovery is surprising since, as mentioned above, European Patent 352 295 of Access Pharmaceuticals reported the requirement for a multivalent binding agent specific for endothelial surface determinants in carriers for drugs and diagnostic agents.

Properties of Biovectors

The Biovector comprises a core of a natural hydrophilic polymer, such as, for example, a cross-linked polysaccharide or a cross-linked oligosaccharide, or a derivative or hydrolysate of a cross-linked polysaccharide or a cross-linked oligosaccharide, or a mixture thereof. The polysaccharide or oligosaccharide may be naturally cross-linked or may be chemically cross-linked by methods known in the art. Some suitable chemical cross-linking methods include, for example, contacting the polysaccharide or oligosaccharide with a multi-functional agent, such as epichlorohydrin or phosphorous oxychloride. The minimum molar ratio of cross-linking agent to glucose residue may be, for example, 1:15, 1:12, or 1:10 in the case of phosphorous oxychloride and 1:50, 1:40, or 1:30 in the case of epichlorohydrin. The maximum molar ratio of cross-linking agent to glucose residue may be, for example, 1:0.5, 1:0.7, or 1:1 in the case of phosphorous oxychloride and 1:2, 1:3, or 1:5 in the case of epichlorohydrin. For epichlorohydrin, a preferred range of ratios of cross-linking agent to glucose residue is 1:15 to 1:7. For phosphorous oxychloride, a preferred range of ratios of cross-linking agent to glucose residue is 1:7 to 1:2. When phosphorous oxychloride is used as the multi-functional agent, the cross-linked product preferably comprises approximately 0.1 to 3.0 mmole phosphate/gram, preferably 0.4 to 1.0 mmole phosphate/gram, of final product.

Figure 1:
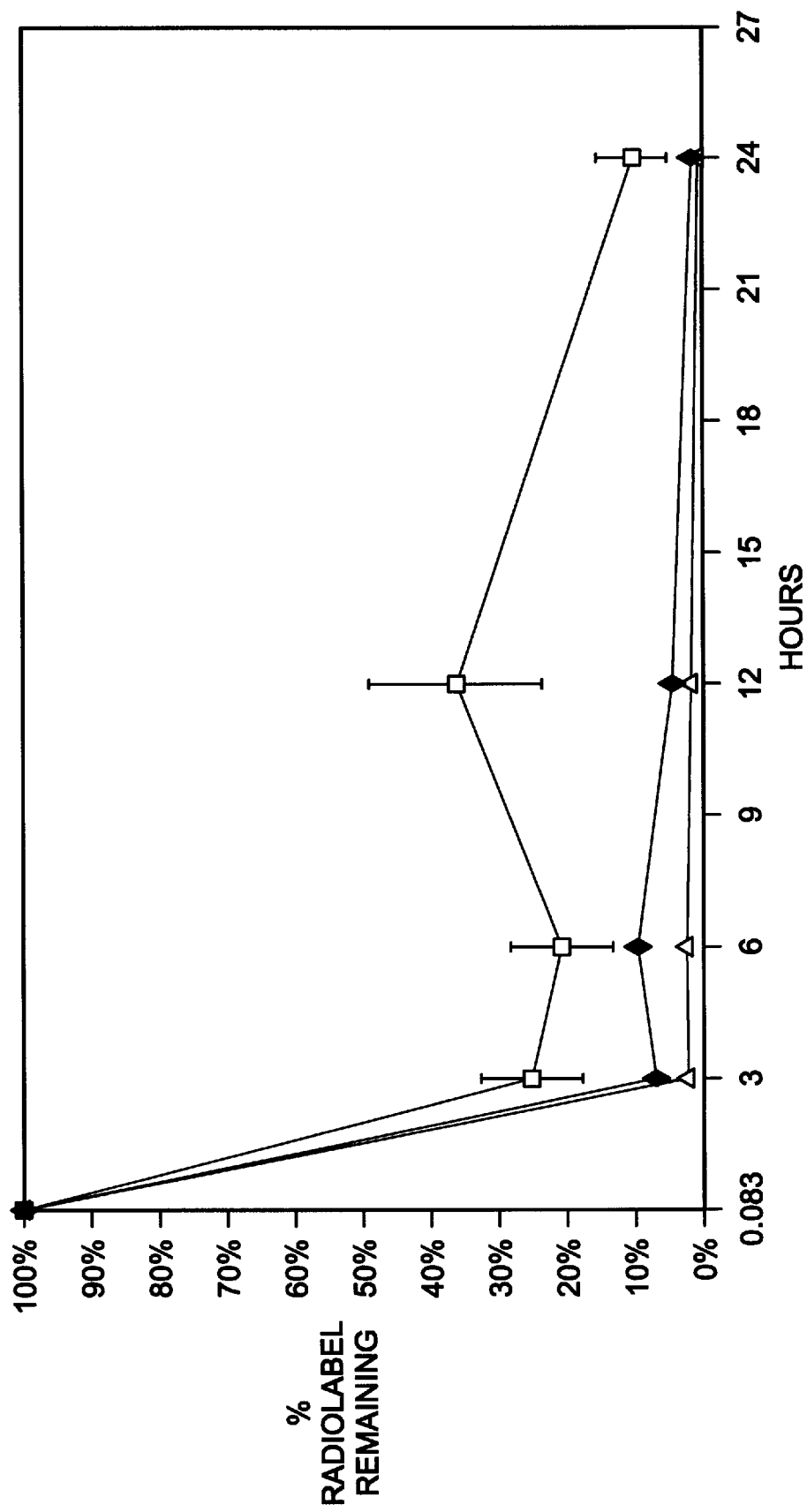
FIG. 1 shows the rate of clearance of $^{14}C$-radiolabeled Biovectors from the nasal mucosa following administration of $^{14}C$-radiolabeled Biovectors to rats. The percent of the $^{14}C$ radiolabel remaining in the nasal turbinate (cavity) is plotted against the number of hours following administration. The protocol is described in Example II. The squares represent cationic Biovectors, the diamonds represent anionic Biovectors, and the triangles represent free $^{14}C$ (control).

Some suitable examples of naturally cross-linked polysaccharides include, for example, cellulose and its derivatives. Some suitable examples of chemically cross-linked polysaccharides include, for example, epichlorohydrin cross-linked starch, i.e. degradable starch microspheres (DSM), and epichlorohydrin cross-linked dextran, i.e. Sephadex.

The polysaccharides or oligosaccharides useful in the present invention may be derived from any saccharide monomer. Glucose is the preferred monosaccharide. The polymers or oligomers may be formed from the monomers in either the α or β orientation, and may be linked at the 1–4 or 1–6 positions of each saccharide unit The polysaccharides or oligosaccharides preferably have a molecular weight between 1,000 to 2,000,000 daltons, preferably 2,000 to 100,000 daltons, and most preferably 3,000 to 10,000 daltons.

The preferred polysaccharides are starch (glucose α 14 polymers) and dextran (glucose α 1–6 polymers derived from bacteria). Starch is especially preferred. Starch from any of the well known sources of starch is suitable. Some suitable sources of starch include, for example, potato, wheat, corn, etc. Other suitable polysaccharides include, for example, pectins, amylopectins, chitosan, and glycosaminoglycan.

The cross-linked polysaccharides or oligosaccharides may also be derivatives of hydrolysates of the cross-linked polysaccharides or oligosaccharides mentioned above. Some preferred hydrolysates of starch include, for example, acid hydrolyzed starch, such as dextrins, or enzyme hydrolyzed starch, such as maltodextrins. The hydrolysis degree of the polysaccharide or oligosaccharide is determined by the reducing power of the hydrolysate, commonly expressed as the Dextrose Equivalent (DE) . The DE range preferably varies between 2 to 20, preferably 2 to 12.

An ionic group (0 to 3 milliequivalents, preferably 0 to 2 milliequivalents, of ionic charge per gram) is optionally grafted to the cross-linked polysaccharide or oligosaccharide. The ionic group may be an anionic group or a cationic group. The Biovectors preferably have a minimum of 0.2, 0.4, 0.6, or 0.8 milliequivalents of ionic charge per gram of polysaccharide core, and a maximum of 1.2, 1.4, 1.6, or 1.8 milliequivalents of ionic charge per gram of polysaccharide core. Methods are known in the art for grafting ionic groups to polysaccharides and oligosaccharides.

The cross-linked polysaccharide or oligosaccharide may be made anionic by grafting a negatively charged or acidic group. Some suitable anionic groups grafted to the polysaccharide or oligosaccharide include, for example, phosphate, sulfate, or carboxylate. The anionic group may be grafted by treating the polysaccharide or oligosaccharide with an activated derivative of a polyhydric acid, such as phosphoric acid, sulfuric acid, succinic acid, or citric acid. Activated derivatives of polyhydric acids include, for example, acyl halides, anhydrides, and activated esters. The preferred anionic group is phosphate grafted via treatment with phosphorous oxychloride. A Biovector to which a phosphate group is grafted is referred to as SMBV-P.

The polysaccharide or oligosaccharide may be made cationic by grafting a ligand that comprises a positively charged or basic group. Some suitable cationic groups grafted to the polysaccharide or oligosaccharide include, for example, quaternary ammonium ions, and primary, secondary, or tertiary amines. Some suitable ligands that can be grafted to the polysaccharide or oligosaccharide include, for example, choline, 2-hydroxypropyltrimethylammonium, 2-dimethylaminoethanol, 2-diethylaminoethanol, 2-dimethylaminoethylamine, and 2-diethylaminoethylamine. These ligands may be conveniently grafted to the polysaccharide or oligosaccharide by methods known in the art, such as, for example, by contacting the polysaccharide or oligosaccharide with a suitable derivative of the respective alkyl group, such as a chloride, bromide, iodide, or epoxide.

Another suitable method for grafting cationic groups to the polysaccharide or oligosaccharide includes grafting a polyhydric acid, as described above, and then using a free acid group, such as a free carboxylate group, to graft the basic ligand via, for example, an amide or ester bond. Amino acids are conveniently grafted this way. Some suitable examples of amino acids include, for example, glycine, alanine, glutamic acid or aspartic acid.

The preferred cationic group is quaternary ammonium. A Biovector to which a quaternary ammonium group is grafted is referred to as SMBV-Q.

It should be noted that Illum et al., International Journal of Pharmaceutics 39, 189–199 (1987), have reported finding no detectable amount of model drugs released from a cationic dextran microsphere, DEAE-Sephadex. Illum et al. attribute this lack of release to binding of the model drug to the cationic binding sites in the microsphere matrix. Applicants have, however, unexpectedly found efficient release of substances from polysaccharides, to which cationic groups have been grafted.

Optionally, the polysaccharide or oligosaccharide core of the Biovector is covalently bonded to a layer of lipid compounds. The layer of lipid compounds may coat the polysaccharide or oligosaccharide core either partially or completely. The lipid layer preferably comprises natural fatty acids, as described in International PCT Application WO 94/23701.

The cross-linked polysaccharide or oligosaccharide, either with or without a lipid layer, may also optionally be partially or completely coated with an outer layer one or more amphiphilic compounds. Such Biovectors are referred to as light Biovectors or L-SMBV. Biovectors consisting only of a core of cross-linked polysaccharide or oligosaccharide are referred to as core Biovectors.

The amphiphilic coating preferably adheres to the cross-linked polysaccharide or oligosaccharide, or to the optional lipid layer, by means of non-covalent bonds, such as by means of ionic or hydrogen bonds. The amphiphilic compounds suitable for the coating are selected to confer a physico-chemical environment appropriate to the substance, the mode of mucosal administration, and the desired effect.

The amphiphilic coating may comprise any amphiphilic compound that can be adsorbed on the surface of the core of the Biovector. Preferably, the amphiphilic coating comprises mainly a natural or synthetic phospholipid or ceramide, or a mixture thereof.

The phosphate group of the phospholipid may optionally be grafted to ionic or neutral groups. Some suitable phospholipids include, for example, phosphatidyl choline, phosphatidyl hydroxycholine, phosphatidyl ethanolamine, phosphatidyl serine, and phosphatidyl glycerol. A preferred phospholipid is dipalmitoyl phosphatidylcholine (DPPC).

The amphiphilic coating may also comprise a derivative of a phospholipid or ceramide. Some suitable derivatives of phospholipids include PEG-phospholipids, and phospholipids grafted to other molecules or polymers.

The amphiphilic coating may also comprise other amphiphilic compounds, either by themselves or in combination with the phospholipids, ceramides, or derivatives described above. Some suitable examples of such other amphiphilic compounds include poloxamers, modified polyoxyethylene, and other detergents and surface active compounds.

Additional compounds and mixtures thereof may be added to the phospholipids or ceramides in the amphiphilic coating. Some examples of such additional compounds include fatty acids, steroids (such as cholesterol), triglycerides, lipoproteins, glycolipids, vitamins, detergents, and surface active agents.

The preparation of Biovectors may normally be conveniently carried out, either as a simple one-step process (in case of a core Biovector) or a as a two step process: the core is first prepared and then is coated with an amphiphilic compound to create a light Biovector.

The size of the Biovector is an important element of the present invention. For example, Illum et al. have emphasized the importance of microspheres having a size larger than 10 $\mu$m for nasal delivery. See Illum et al., International Journal of Pharmaceutics 39, 189–199 (1987).

Applicants have, however, unexpectedly found that Biovectors much smaller than 10 um are highly efficient carriers for administering substances to the nasal mucosa, as well as to other mucosa. The Biovectors of the present invention preferably have a minimum diameter of about 20 nm, more preferably about 30 nm, and most preferably about 40 nm. The maximum size of the Biovectors is about 200 nm, more preferably about 150 nm, and most preferably about 100 nm. The optimal size of the Biovector is between 60–90 nm, and most optimally about 80 nm.

The relatively small size of the Biovectors confers various advantages, making the Biovectors even more suitable for administration to the mucosa. For example, the Biovectors have larger relative surfaces and volumes than larger nanospheres and microspheres. In addition, the small size of the Biovectors permit convenient sterilization by microfiltration, thereby avoiding the need for preservatives.

The Biovectors can be administered in various forms. For example, the Biovectors can be administered in dispersed form, such as suspensions or gels. The Biovectors can also be produced in dry form by methods known in the art, and administered in a suitable metered-dosing device.

For example, a suspension or gel of dispersed Biovectors can be dried by lyophilization or spray drying. All light Biovectors, such as anionic and cationic light Biovectors, as well as all core Biovectors, such as anionic and cationic core Biovectors, can be dried. The Biovectors may be administered in dry form, or may be resuspended (i.e. rehydrated) in a suitable medium, preferably a pharmaceutically acceptable aqueous liquid or gel, and administered. For the purposes of this application, resuspended Biovectors mean Biovectors that have been dried and resuspended in a suitable medium.

Substances for Mucosal Administration

The substance administered to a mammal in combination with a Biovector in accordance with the present invention may be any substance that is administered to a mammal. Some suitable substances include, for example, therapeutic agents, prophylactic agents, and diagnostic agents. A substance may be introduced for more than one purpose, such as, for example, as combination therapeutic and prophylactic agents, prophylactic and diagnostic agents, and therapeutic and diagnostic agents.

The therapeutic agent may be any composition of matter used in the treatment of diseases and conditions that afflict mammals. Some suitable examples of therapeutic agents include a radiopharmaceutical, an analgesic drug, an anesthetic agent, an anorectic agent, an anti-anemia agent, an anti-asthma agent, an anti-diabetic agent, an antihistamine, an anti-inflammatory drug, an antibiotic drug, an antimuscarinic drug, an anti-neoplastic drug, an antiviral drug, a cardiovascular drug, a central nervous system stimulator, a central nervous system depressant, an anti-depressant, an anti-epileptic, an anxyolitic agent, a hypnotic agent, a sedative, an anti-psychotic drug, a beta blocker, a hemostatic agent, a hormone, a vasodilator, a vasoconstrictor, a vitamin, etc.

The prophylactic agent that is administered to a mammal in combination with a Biovector according to the invention may be any prophylactic agent used for preventing or reducing the effect of any disease or condition that afflicts mammals by any mechanism. For example, the prophylactic agent may be an antigen used in a vaccine against a pathogen. The pathogen may, for example, be a virus or a microorganism, such as a bacterium, a yeast, or a fungus. The virus may, for example, be an influenza virus, such as Haemophilus influenzae; a cytomegalovirus; HIV; a papilloma virus; a respiratory syncytial virus; a poliomyelitis virus; a pox virus, such as chicken pox virus (i.e. varicella zoster virus); a measles virus; an arbor virus; a Coxsackie virus; a herpes virus, such as herpes simplex virus; a hantavirus; a hepatitis virus, such as hepatitis A, B, C, D, E, or G virus; a lyme disease virus, such as Borrelia burgdorferi; a mumps virus, such as Paramyxovirus; or a rotavirus, such as A, B, or C rotavirus. Particularly good results have been obtained with vaccines against influenza virus and HIV.

A bacterium against which a vaccine according to the present invention is effective may be any bacterium capable of causing disease in mammals. For example, the bacterium may be a member of the genus Neisseria, such as *N. gonorrhoeae and N. meningitidis*; Aerobacter; Pseudomonas; Porphyromonas, such as *P. gingivalis*; Salmonella; Escherichia, such as *E. coli*; Pasteurella; Shigella; Bacillus; Helibacter, such as *H. pylori*; Corynebacterium, such as *C. diphteriae*; Clostridium, such as *C. tetanii*; Mycobacterium, such as *M. tuberculosis* and *M. leprae*; Yersinia, such as *Y. pestis*; Staphylococcus; Bordetella, such as *B. pertussis*; Brucella, such as *B. abortus*; Vibrio, such as *V. cholerae*; and Streptococcus, such as mutants Streptococci.

Other pathogens against which a vaccine according to the present invention is effective include, for example, a member of the genus Plasmodium, such as the species that causes malaria; a member of the genus Schisostoma, such as the species that causes Schisostomiasis or Bilharzia; and a member of the genus Candida, such as *C. albicans.*

The substance that can be combined with a Biovector may be a diagnostic agent. The diagnostic agent may be any composition of matter that is introduced into a mammal for the purpose of detecting any disease or condition, or to detect the concentration of a different substance added to the mammal, such as a drug or a vaccine. For example, the diagnostic agent may be a contrast agent or an imaging agent, including a magnetic imaging agent, that is capable of detecting an organ or other internal part of the body of the mammal. Alternatively, the diagnostic agent may be capable of detecting irregularities within the mammal, such as irregularities of the cornea, the respiratory tract, the digestive tract, the auditory canal, the urethra, the rectum, or any other part of a mammal containing a mucosal membrane.

For the above purposes, the diagnostic agent is advantageously labeled with a detectable group. The detectable group may, for example, be a radioactive group; a fluorescent group, such as, for example, fluorescene; a visible group, such as, for example, a marker dye; or a magnetic group, preferably suitable for magnetic resonance imaging.

The substance to be delivered in combination with a Biovector may, for example, be a small chemical molecule or a biological molecule. A small chemical molecule is usually a non-polymeric molecule that may or may not occur naturally in the mammal to which it is administered. The small chemical molecule may, for example, be an organic molecule, an inorganic molecule, or an organo-metallic molecule. Some examples of small chemical molecules include steroids, porphyrins, nucleotides, nucleosides, etc. as well as mixtures, and derivatives thereof.

Biovectors are particularly effective in delivering biological molecules to the mucosa For the purposes of this specification, a biological molecule is a polymer of a type that occurs in nature, or a monomer or moiety thereof. Such polymers typically comprise monomers such as amino acids, nucleosides, nucleotides, and saccharides, and mixtures thereof. Some structural classes of biological molecules include, for example, amino acids, peptides, proteins, glycoproteins, and lipoproteins; proteoglycans; monosaccharides, oligosaccharides, polysaccharides, and lipopolysaccharides; fatty acids, including eicosanoids; lipids, including triglycerides, phospholipids, and glycolipids.

Additional biological molecules that can be delivered to the mucosa by means of Biovectors include nucleotides, nucleosides, and nucleic acid molecules, including DNA and RNA polymers and oligomers. The nucleic acids may be, for example, ribozymes and antisense oligonucleotides. Nucleic acids may be administered for their own diagnostic or therapeutic potential, or for their ability to be expressed in connection with gene therapy.

Some functional classes of biological molecules include, for example, cytokines, growth factors, enzymes, antigens, (including epitopes of antigens and haptens), antibodies, hormones (including both natural and synthetic hormones and their derivatives), co-factors, receptors, enkephalins, endorphins, neurotransmitters, and nutrients. Some specific examples of biological molecules include, for example, insulin, an interferon, such as an $\alpha$-, $\beta$-, or $\gamma$-interferon; an interleukin, such as any of IL-1 to IL-15; any of the interleukin receptors, such as IL-1 receptor; calcitonin; growth factors, such as erythropoietin, thrombopoietin, epidermal growth factor, and insulin-like growth factor-1.

Administration of the substance in accordance with the present invention may be accompanied by one or more supplementary compound for enhancing the activity, properties, or marketability of the substance. For example, adjuvants that enhance the absorption efficiency of the mucosa are known in the art. Some examples of such mucosa absorption enhancers include, for example, bile salts, such as sodium glycocholate, and surfactants, such as polyoxyethylene-9-lauryl ether. Adjuvants for enhancing the immunogenicity of antigens are also known. Some examples of immunogenicity enhancers include, for example, MPL, Quil A, QS 21, LPS, endotoxins, CTB, and BCG. Some additional supplementary compounds include, for example, disinfectants, preservatives, surfactants, stabilizing agents, chelating agents, and coloring agents.

Another important feature of the present invention is the flexibility in administering substances to the mucosa. For example, unlike most other pharmaceutical carriers, the present invention provides for the delivery of more than one substance per Biovector to be delivered to a mucosal surface.

There is also flexibility in where the one, or more than one, substance is located in the Biovector. For example, the one, or more than one, substance may be located in the inner core of the cross-linked polysaccharide or oligosaccharide. Alternatively, the one, or more than one, substance may be located at the outer surface of the cross-linked polysaccharide or oligosaccharide.

If the cross-linked polysaccharide or oligosaccharide is coated with an amphiphilic layer, the one, or more than one, substance may be located in the inner core of the amphiphilic compound layer. Alternatively, the one, or more than one, substance may be located at the outer surface of the amphiphilic compound layer.

If more than one substance per Biovector is administered to a mammal, some or all of the substances may be located in the same part of the Biovector. Alternatively, some or all of the substances may be located in the different parts of the Biovector.

Methods are known for directing substances to various parts of Biovectors. See International PCT Application WO94/20078.

As with other carriers, the substance may be pre-loaded in a Biovector, and the loaded Biovector stored prior to administration to the mammal. Preferably, however, the substance is post-loaded on an empty Biovector just prior to packaging or, such as in the case of labile substances for example, the Biovector may be used as the dilution media for entraping the substance just prior to administration to the mammal. Methods are known for pre-loading and post-loading Biovectors. See, for example, International PCT Applications WO 94/20078, WO 94/23701, and WO 96/06638 of Biovector Therapeutics S.A.

Advantages of Mucosal Administration with Biovectors

Some of the advantages of the mucosal administration of substances to mammals may be seen by reference to the examples below. These advantages are described for illustrative reasons only. The present invention is not, however, in any way limited by the examples.

As shown in the experiment described in Example II, for example, the ionic groups permit the mode of administration of Biovectors to be varied according to the requirements of a particular case. The protocol is described in detail in Example II. Briefly, three cationic formulations and three anionic formulations of $^{14}C$-labeled Biovectors were administered intranasally to rats. At various times, the rats were sacrificed, and the percent of the label remaining in the nasal cavity and in the plasma was determined.

The results of this experiment, which are shown in FIG. 1, demonstrated that approximately 30% of the dose of three cationic Biovectors administered intranasally to rats remained in the nasal cavity five minutes after administration, and was still present after twelve hours.

The good mucoadhesion of the cationic Biovectors increased the residence time of the Biovector in the target mucosa. The increased residence time is important where increased bioavailability or a local effect of the administered substance is desired. A local effect of the administered substance is desired under a variety of circumstances.

For example, a local effect is desired when an antibiotic or antiviral drug is administered to treat a local bacterial or viral infection. Alternatively, a local effect is desired when a vaccine is administered to protect a mammal against a mucosal infection by a microorganism or virus. A third example of a situation where one desires a local effect is the administration of a diagnostic agent to image an organ that contains a mucosal membrane.

By contrast, the anionic Biovectors (SMBV-P1, SMBV-P2, and SMBV-P3), which exhibit comparable initial mucoadhesion (five minutes), have a more rapid clearance from the nasal mucosa than the cationic Biovectors. With the anionic Biovectors, less than 10% of the dose remaining five minutes after administration was found in the nasal cavities three hours after administration. There was no significant variation for the three anionic formulations tested.

Figure 2:
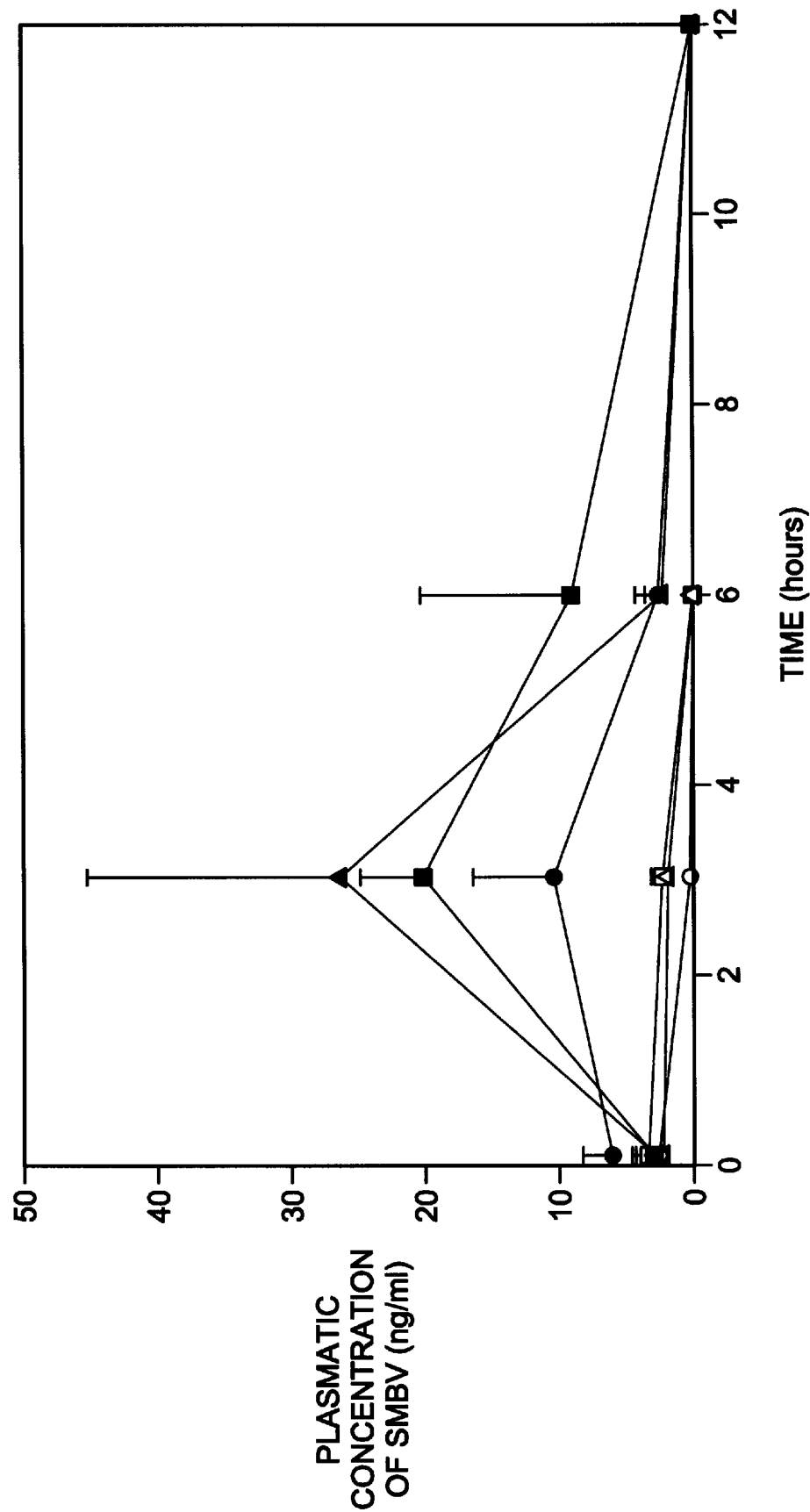
FIG. 2 shows the concentration in ng/ml of the radiolabel found in the plasma three, six, and twelve hours following administration of $^{14}C$-radiolabeled Biovectors to rats in accordance with the protocol described in Example II. The filled triangles represent SMBV-P1, the filled circles represent SMBV-P2, the filled squares represent SMBV-P3, the empty triangles represent SMIV-Q1, the empty circles represent SMBV-Q2, and the empty squares represent SMBV-Q3.

A significant amount of labeled anionic Biovectors was, however, found in the plasma three hours and, to a lesser extent, six hours after nasal administration of SMBV-P1, SMBV-P2, and SMBV-P3, respectively. See Example II and FIG. 2. Therefore, anionic Biovectors are of particular use when a systemic response is desired.

In general, there are advantages in using positively charged Biovectors for administering Biovectors that have enhanced mucosal residency times. There are advantages in administering negatively charged Biovectors that have enhanced ability to pass through the mucosa to the blood stream. The advantages of both charge types of Biovectors can be combined by administering a mixture of a positively charged Biovector and a negatively charged Biovector.

The results of Example III confirm that in-vivo behavior of anionic Biovectors (SMBV-P1, SMBV-P2, and SMBV-P3) is different from that of cationic Biovectors (SMBV-Q1, SMBV-Q2, and SMBV-Q3). In this experiment, rats treated in accordance with the protocol of Example 2 were sacrificed after twelve hours, and the $^{14}C$ remaining in various organs was measured.

As expected, the relatively large amounts of $^{14}C$ from cationic Biovectors found in the nasal cavities, nasal cavity washings, and bronchi indicate an increased residence time of cationic Biovectors in the mucosa in which, or near which, the Biovectors are administered. For the anionic Biovectors, the significant amount of $^{14}C$ found in the liver and kidney demonstrates the increased trans-mucosal passage of the Biovectors into the bloodstream.

The large amount of $^{14}C$ from both cationic and anionic Biovectors found in the small and large intestine indicates that elimination of Biovectors following nasal administration occurred through the digestive tract. The increase in the residence time of Biovectors in the digestive tract is especially significant for the oral administration of antigens associated with Biovectors in the case of oral vaccination.

Further evidence for the good mucoadhesion of the cationic Biovectors is demonstrated by the results shown in Example IV. In this experiment, fluorescein-labeled cationic light Biovectors as either dispersed or resuspended suspensions were administered intranasally to rats. Approximately 20% of the resuspended Biovectors adhere to the mucosa upon administration, and the same amount remains for at least twelve hours. The dispersed Biovectors do not adhere to the nasal mucosa after three hours, except at low levels. Approximately one third of the administered fluorescent Biovectors are still found in suspension in the nasal washing five minutes after administration, but none is found six hours later.

Example V provides important evidence of the superiority of Biovectors in the mucosal administration of vaccines. In this experiment, a comparison was made between the intranasal (i.n.) administration of a monovalent split antigen of hemagglutinin (HA) and neuraminidase (N) prepared from viral membranes in cationic light Biovectors with the intranasal and subcutaneous (s.c.) administration of antigen alone. The experiment demonstrates that the antigen administered i.n. in a Biovector is able to elicit a superior mucosal and seric response.

Thus, the total IgG, specific IgG and inhibitory hemagglutination were at the same order of magnitude when the antigen was administered i.n. in a Biovector compared to antigen administered s.c. alone. However, the antigen/Biovector formulation induces the production of circulating and secretory IgA, while the antigen alone administered s.c. or i.n., for practical purposes, did not.

Moreover, the ratio of specific IgG to total IgG in the nasal washing was twice as high when the antigen was administered i.n. in a Biovector than when the antigen was administered alone s.c. A higher ratio means that the immune response is expected to be more specific and more protective. While not wishing to be bound by any theory, applicants believe that membrane antigens such as those used in this experiment are presented by the outer layer of the Biovector, creating a lipid surrounding favorable for presenting the antigen to the immune system.

The experiment described in Example VI compares the effect of different formulations of the gp160 protein of HIV on the mucosal immune response of rabbits. The protein was administered with two formulations of a positively charged light Biovector, a dispersed formulation and an resuspended formulation. As a control, the protein was administered in combination with a potent mucosal adjuvant, subunit B of cholera toxin (CTB). In each of the three cases, a series of immunizations were made at thirty day intervals. The first two immunizations were vaginal, the second two immunizations were oral, and the final immunization was intramuscular.

The results showed that the Biovectors were at least as efficient as CTB in inducing specific IgA secretions in the vagina and in saliva ten days after the second vaginal administration, ($D_{40}$). The resuspended SMBVs induced a 50% increase of the IgAs when compared to formulations of the antigen with CTB or in dispersed SMBV.

It should be noted that vaginal administration of the antigen induced secretion of :specific IgAs in the saliva as well as in the vagina. Thus, the antigen, which entered the MALT (mucosal-associated lymphoid tissue) at the vaginal level, induced the secretion of IgAs in situ. In addition, the Biovector formulations were able to stimulate a robust IgA response in the saliva by entering the so-called "common mucosal immune system."

The experiment described in Example VII compares the intranasal immunization of mice with influenza hemagglutinin in a control formulation with that of four formulations of light Biovectors: dispersed and positively charged, dispersed and negatively charged, resuspended and positively charged, and resuspended and negatively charged. The effect of pre-loading and post-loading each Biovector formulation on the relative serum IgG titer after 28 days was measured.

In addition, a comparison of the relative titer obtained by administering the pre-loaded Biovectors to animals that were awake with that obtained by administering the pre-loaded Biovectors to animals that were anesthetized was made.

As expected, the control subunit antigen without any carrier or adjuvant is not very immunogenic when administered intranasally to mice, either anesthetized or awake. Of the SMBV subgroups, the positively charged and dispersed Biovectors showed a significant improvement (by more than an order of magnitude) of the titer over those obtained with the antigen alone or other Biovector formulations. Both the pre-loaded and post-loaded Biovectors have generally comparable effects. This versatility of the Biovector can be of particular interest, allowing either a mixing of the active substance with the Biovector upon administration, or integration of the active substance with the Biovector prior to its use.

Surprisingly, the anesthetized animals did not show a significant increase in antibody titers, suggesting that the deposition, if any, of the antigen in the lower respiratory tract or the lung had little biological effect.

EXAMPLES

Example I

Preparation of Biovectors.

In the examples below, Biovectors, when labeled, are labeled before the phospholipidation process. When loaded with one (or more than one) biologically active compound, the loading occurs after the process of manufacturing the empty Biovector.

I(a). Preparation of anionic core Biovector (SMBV-P1)

500 g of maltodextrin (Glucidex, Roquette, Lestrem, France) are poured in a 10 liter reactor (TRIMIX) along with 2 liters of demineralized water. After solubilization at 4° C., 500 ml of sodium hydroxide (NaOH) 10M are added with mechanical stirring. When the temperature of the solution has stabilized at 4° C., 1700 ml of 10M NaOH and 283.3 ml of $POCL_3$ are added under controlled flow conditions. The cross linking reaction takes place with mechanical stirring during a 20 hour period. At the end of the 20 hour period, the reacting mixture is stirred an additional 15 minutes. A volume of 5 liters of demineralized water is added and the pH is adjusted to 7.0 by neutralization with glacial acetic acid. The hydrogel obtained is ground under high-pressure. At the end of this step, the mean diameter of the particles is approximately 60 nm. Further purification proceeds as follows: (I) microfiltration at 0.45 $\mu$m to eliminate larger particles, (ii) diafiltration at constant volume to eliminate smaller molecules (salts, fragments of polysaccharides, etc). The anionic polysaccharide cores (PSC) are then concentrated, added to sterile flasks, and stored at ~20° C.

I(b). Preparation of dispersed anionic light Biovector (SMBV-P2)

Anionic core Biovectors are prepared as described in Example I(a), and labeled as described when necessary. Thawed cores are diluted in osmosed water in a glass flask at a concentration of 1 mg per milliliter (e.g. 250 mg of PSC/250 ml of water). The dispersion is stirred 5 to 10 minutes and homogenized in a high pressure homoginizer (RANNIE Lab) at 400 bars for 3 minutes. The suspension is warmed at 80° C. in a thermostated bath. The lipids of the future outer membrane (e.g. DPPC, DPPC/cholesterol, etc), in powder form, are added in a ratio of 0.3:1 (w/w) of the PSC mass (e.g. 75 mg of lipids for 250 mg of PSC). The lipids are mixed and solubilized in 2.5 ml of ethanol 95% (v/v). The homogenizer is warmed to 60° C. by closed water circulation. The ethanol solution of lipids is injected in the suspension of PSC at 80° C. and then homogenized at 450 bars for 25 minutes at 60° C. At the end of this step, the preparation is put in a glass container and free ethanol is eliminated from the light-Biovector preparation at reduced pressure. The resulting light anionic Biovectors are filtered (0.2 $\mu$m) and stored.

I(c). Preparation of resuspended anionic light Biovector (SMBV-P3)

Anionic core and light Biovectors are suspended in water at a concentration of 1.2 mg/ml, and then distributed in doses of 1 ml in cryovials especially designed for freeze-drying. The cryovials are placed on a freeze-dryer, (Dura dry, FT Systems), frozen at –30° C., and freeze dried in stages, first –10° C., then 0° C., and finally 10° C. during the primary drying, and 30° C. for the following step. Drying is usually achieved in 24 hours. The lyophilized Biovectors in each cryovial are rehydrated in 200 $\mu$l of PBS.

I(d). Preparation of cationic core Biovector (SMBV-Q1)

500 mg of maltodextrine (Glucidex, Roquette, Lestrem, France) are solubilized with 0.880 liters of water at 20° C., with stirring, in a thermoregulated reactor. Seven grams of $NaBH_4$ are added and mixed for 1 hour. 220 ml of NaOH 10M are added, followed by 30.25 ml of epichlorydrin (Fulka). After 12 hours of reaction, 382.3 g of glycidyltrimethylammonium chloride (Fulka) are introduced and the mixture is stirred for 10 hours. The resulting gel is diluted with 8 liters of demineralized water and the pH is adjusted to 7.0 by neutralization with glacial acetic acid. The hydrogel obtained is ground under high-pressure. The pressure used is 400 bars. At the end of this step, the mean diameter of the particles is approximately 60 nm. Further purification proceeds as follows: (I) microfiltration at 0.45 $\mu$m to eliminate larger particles, (ii) diafiltration at constant volume to eliminate smaller molecules (salts, fragments of polysaccharides). The cationic PSC are then concentrated, sampled in sterile flasks and stored at ~20° C.

I(e). Preparation of dispersed cationic light Biovector (SMBV-Q2)

Cationic core Biovectors are prepared as described in Example I(d), and labeled as described when necessary. Thawed cores are diluted in osmosed water in a glass flask at a concentration of 1 mg per milliliter (e.g. 250 mg of PSC/250 ml of water). The dispersion is stirred 5 to 10 minutes and homogenized (RANNIE Lab) at 400 bars for 3 minutes. The suspension is warmed at 80° C. in a thermostated bath. The lipids of the future outer membrane (e.g. DPPC, DPPC/cholesterol, etc), in powder form, are added in a ratio of 0.3:1 (w/w) of the PSC mass (e.g. 75 mg of lipids for 250 mg of PSC). The lipids are mixed and solubilized in 2.5 ml of ethanol 95% (v/v). A homogenizer is warmed to 60° C. by closed water circulation. The ethanol solution of lipids is injected in the suspension of PSC at 80° C. and then homogeneized at 450 bars during 25 minutes at 60° C. At the end of this step, the preparation is put in a glass container and free ethanol is eliminated from the light Biovector preparation at reduced pressure. Light cationic Biovectors are filtered (0.2 $\mu$m) and stored.

I(f). Preparation of resuspended cationic light Biovector (SMBV-Q3)

Cationic core and light Biovectors are suspended in water at a concentration of 1.2 mg/ml, and then distributed in doses of 1 ml in cryovials especially designed for freeze-drying. The cryovials are placed on a freeze-dryer, (Dura dry, FT Systems), frozen at -30° C., and freeze dried in stages, first –10° C., then 0° C., and finally 10° C. during the primary drying, and 30° C. for the following step. Drying is usually achieved in 24 hours. The lyophilized Biovectors in each cryovial are rehydrated in 200 µl of PBS.

I(g). Labeling of Biovectors with $^{14}C$ cyanuric chloride

Polysaccharidic cores are labeled with radioactive $^{14}C$ triazine using the ability of cyanuric chloride to react with the free hydroxyl groups of the polysaccharide. This reaction is carried out on the finished polysaccharide cores prepared as described above. The protocol below is representative of any polysaccharide core (anionic or cationic).

$^{14}C$ cyanuric chloride at 47 mCl/mmol is obtained following custom synthesis from Dupont NEN Product (Boston, Mass.). The cyanuric chloride is suspended before use in pure acetonitrile at 100 g/l. The polysaccharide cores are suspended in water at 40 g/l, and the pH is adjusted to 10 with sodium carbonate. The suspension is warmed and maintained at 50° C. The desired quantity of cyanuric chloride is added (normally between 1–5% w/w to polysaccharide cores) and the pH is monitored with a pH-meter. The pH is maintained during the reaction by adding small portions of solid sodium carbonate and the reaction is carried out during a period of five hours. Once the reaction is completed, the labeled polysaccharide core suspension is placed in a ultrafiltration stirred cell equipped with a 10 Kilodalton membrane (Amicon, France) and the solution is diafiltered against 1 mM pH 7.4 phosphate buffer solution until no radioactivity is found in the filtrate. The resulting suspension of labeled polysaccharide cores is then sterilized by filtration through 0.2 μm filters and stored in sterile containers. The radioactivity contents is determined by measurements on a Beckman Beta-Counter (Germany) and expressed in μCi per mg of polysaccharide cores. The resulting labeled polysaccharide cores can be used as described above to prepare labeled Biovectors.

I(h). Labeling of Biovectors with dichlorotriazinyl fluorescein.

Polysaccharide cores are labeled with dichlorotriazinylfluorescein using the ability of the dichlorotriazine moiety to react with the free hydroxyl groups of the polysaccharide. This reaction is carried out on the finished polysaccharide cores prepared as described above. The protocol is representative of any polysaccharide core (anionic or cationic at any charge). Dichlorotriazinyl fluorescein is obtained from Sigma Chemicals (St. Louis, USA). The dichlorotriazinyl fluorescein is suspended before use in pure dimethyl formamide at 100 g/liter. The polysaccharide cores are suspended in a buffer solution (150 mM NaCl and 140 mM sodium hydrogen carbonate) at 50 grams/liter and the pH is adjusted to 10 without sodium hydroxide. The desired quantity of dichloro-triazinylfluorescein is added (normally between 1–5% w/w to polysaccharide cores) and the reaction is allowed to stand five hours at room temperature with gentle stirring. Once the reaction is finished, the labeled polysaccharide core suspension is placed in an ultrafiltration stirred cell equipped with a 30 kd membrane (Amicon, France), and the solution is diafiltered against water until no fluorescence is found in the filtrate. The resulting labeled polysaccharide core suspension is then sterilized by filtration on 0.2 μm filters and conditioned on sterile containers. The fluorescence content is determined by measurements on a Perkin Elmer Luminescence Spectrophotometer LS 50 B. The resulting polysaccharide cores can be normally used after labeling to prepare SMBV suspensions as described above.

I(i). Preparation of $^{111}$Indium formulation of SMBV Q2

A solution of $^{111}InCl_3$ (Cisbio)(370 MBq/ml) was mixed with an $InCl_3$ (Fluka) solution ($InCl_3$ 15 mM, sodium citrate 2 mM, ph 6.0). This solution was added to an SMBV-Q2 suspension. The final suspension had the following characteristics: SMBV-Q2 15 mg/ml, $InCl_3$ 0.3 mM, sodium citrate 1 mM, pH 6.0.

The free indium concentration was measured with a gamma counter after 1/10 dilution in a citrate buffer (1 mM, pH 6.0) and ultrafiltrated on Microcon 100 kd (Amicon). The resulting suspension was sterilized by filtration (0.2 μm), and maintained at 4° C., until it was administered. For administration of the suspension to the subject, 120 Il of the suspension was introduced in a monospray (Peiffer, UK), thereby allowing the administration of 100 μl/spray.

Table I-1, shown below, summarizes the results of a human pharmacokinetics study utilizing the prepared batches. Under these conditions, the labeling of SMBV by $InCl_3$ was extremely quantitative with association ratios of 87.5±9.8%. Furthermore, the radioactivity dosages (0.39±0.03 MBq/dose) was found to be perfectly compatible with a scintigraph taken after human nasal administration of SMBV.

TABLE I-1

Characteristics of the SMBV-Q2 preparations labeled with $^{111}$In used in human pharmacokinetics study

| | Average | SD |
|---|---|---|
| PSC (mg/ml) | 12.7 | 1.7 |
| DPPC (mg/ml) | 2.3 | 0.2 |
| Cholesterol (mg/ml) | 0.67 | 0.06 |
| Radioactivity (Mbq/dose) | 0.39 | 0.03 |

I(j). Large scale preparation of dispersed light Biovectors

Modifications may be made to the procedures described in Examples I(b) and I(e) to assist in scaling up the procedures. The duration times of the high pressure homogenization steps are varied on the basis of the volume and the concentration of light Biovectors to be prepared. The second high pressure homogenization step may be eliminated, and replaced by incubation of the light Biovectors at 80° C. with stirring. The elimination of ethanol may be accomplished by means of diafiltration against water rather than at reduced pressure.

Example II

Adhesion of $^{14}C$-Labeled Biovector on Nasal Mucosa of Rats.

Male Sprague Dawley rats of approximately 200 g each were divided into six groups according to the type of labeled Biovector administered. The six types of Biovector are summarized in Table II-1 below:

TABLE II-1

| Samples | SMBV-P1 | SMBV-P2 | SMBV-P3 | SMBV-Q1 | SMBV-Q2 | SMBV-Q3 |
|---|---|---|---|---|---|---|
| Type | Core | Light | Light | Core | Light | Light |
| Example | I(a) | I(b) | I© | I(d) | I(e) | I(f) |
| Charge type | Anionic | Anionic | Anionic | Cationic | Cationic | Cationic |

TABLE II-1-continued

| Samples | SMBV-P1 | SMBV-P2 | SMBV-P3 | SMBV-Q1 | SMBV-Q2 | SMBV-Q3 |
|---|---|---|---|---|---|---|
| PSC Charge | 1.79 mEq/g | 1.79 mEq/g | 1.79 mEq/g | 1.85 mEq/g | 1.85 mEq/g | 1.85 mEq/g |
| PSC mean diameter | 55 nm | 55 nm | ND | 68 nm | 68 nm | ND |
| State | Dispersed | Dispersed | Resuspended | Dispersed | Dispersed | Resuspended |

Characteristics of Biovectors used for intranasal pharmacokinetic and biodistribution studies. PSC Charge refers to the milliequivalents of ionic charge per gram of polysaccharide core.
ND means not determined.

Each rat in groups SMBV-P1 and SMBV-Q1 received a dose of 100 μg of its respective $^{14}$C-labeled Biovector formulation administered intranasally without anesthetic in a volume of 50 μl of suspension (25 μl in each nostril).

Each rat in groups SMBV-P2, SMBV-P3, SMBV-Q2, and SMBV-Q3 received a dose of 150 μg of its respective $^{14}$C-labeled Biovector formulation administered without anesthetic intranasally in a volume of 50 μl of suspension (25 μl in each nostril).

The above doses represent approximately 200 μl of suspension of Biovectors per kg of rat. This volume of suspension is equivalent to approximately 400 μg of polysaccharide and approximately 200 μg of lipid per kg of rat.

At 0.083 hours (five minutes), three hours, six hours, twelve hours, and twenty four hours, three rats in each group were sacrificed. Both nasal cavities were isolated; the nasal tract was opened and washed with 5 ml of physiological saline; and blood was taken and centrifuged. The $^{14}$C remaining in the nasal washing, nasal cavity, and plasma were measured. The results are shown in Figures A and B.

Example III

Biodistribution of $^{14}$C-Labeled Biovector After Nasal Administration.

Male Sprague Dawley rats of approximately 200 g each were treated as described in Example II. Twelve hours after nasal administration, three rats per sample were sacrificed, and the $^{14}$C remaining in the liver, spleen, kidney, blood, bronchi, lung, oesophagus, stomach, small and large intestine, skeletal muscle, sub-maxillary lymph node, brain, and nasal turbinate was measured.

Table III-1 below summarizes the biodistribution twelve hours after nasal administration of the Biovector formulations described in Table II-1.

TABLE III-1

| Organs | SMBV-P1 | SMBV-P2 | SMBV-P3 | SMBV-Q1 | SMBV-Q2 | SMBV-Q3 |
|---|---|---|---|---|---|---|
| Bronchi | blq | blq | blq | 1.05 ± 1.81 | blq | 1.34 ± 1.53 |
| Lung | blq | blq | blq | blq | blq | 0.15 ± 0.11 |
| Esophagus | 0.05 ± 0.04 | blq | blq | blq | blq | blq |
| Stomach | 0.23 ± 0.08 | 0.44 ± 0.48 | 0.38 ± 0.41 | 0.55 ± 0.18 | 1.56 ± 0.98 | 3.20 ± 4.60 |
| S-L Intestine | 46.9 ± 8.1 | 48.6 ± 16.7 | 43.0 ± 19.5 | 42.0 ± 8.7 | 52.3 ± 21.5 | 33.4 ± 16.1 |
| Spleen | blq | blq | blq | blq | blq | blq |
| Liver | 0.72 ± 0.49 | 0.46 ± 0.03 | 0.33 ± 0.06 | blq | blq | blq |
| Kidney | 0.31 ± 0.16 | 0.34 ± 0.14 | 0.23 ± 0.02 | 0.04 ± 0.01 | 0.04 ± 0.01 | blq |
| Brain | blq | blq | blq | blq | blq | blq |
| Muscle | blq | blq | blq | blq | blq | blq |
| Lymph Node | blq | blq | blq | blq | blq | blq |
| Plasma | blq | blq | blq | blq | blq | blq |
| Turbinate | 0.54 ± 0.64 | 0.68 ± 0.90 | 0.51 ± 0.54 | 11.4 ± 7.0 | 8.7 ± 8.8 | 8.6 ± 7.4 |
| Washing Fluid | 0.007 ± 0.002 | 0.008 ± 0.003 | 0.008 ± 0.002 | 0.64 ± 1.03 | 0.25 ± 0.20 | 0.26 ± 0.38 |

Twelve hours biodistribution after nasal administration of different Biovector formulations. The Biovectors are described in Table II-1 above.
Blq = below level of quantification.

Example IV

Adhesion of Fluorescent Biovectors to the Nasal Mucosa of Rats.

Three groups of anesthetized Males Wistar rats (twelve rats in each group) received a single drop in the nostrils of 50 μl of either a suspension of PBS/glycerol (control); a suspension of 0.93 mg/ml of fluorescein-labeled cationic light Biovectors (Example I(h)) suspended in PBS/glycerol (dispersed L-SMBV); or a suspension of 0.93 mg/ml of lyophilized cationic fluorescein-labeled light Biovectors re-suspended in PBS/glycerol (resuspended L-SMBV). The dispersed SMBV have diameters of approximately 80 nm, and polysaccharide cores grafted with quaternary ammonium ions.

At times zero, five minutes, three hours, six hours, and twelve hours, two rats from each group were sacrificed. The fluorescence was measured from both the nasal washings (three washings with NaCl) and in the nasal mucosa (scratching). The results are shown in the Tables IV-1 and IV-2 below.

TABLE IV-1

Percent of fluorescence remaining in the nasal washings

| NASAL WASHINGS | 5 min. | 3 hr. | 6 hr. | 12 hr. |
|---|---|---|---|---|
| disp. SMBV-Q | 28% | 3% | 0% | 0% |
| res. SMBV-Q | 30% | 1% | 0% | 0% |

TABLE IV-2

Percent of fluorescence remaining in the nasal cavity

| NASAL MUCOSA | 5 min. | 3 hr. | 6 hr. | 12 hr. |
|---|---|---|---|---|
| disp. SMBV-Q | 40% | 4% | 3% | 0% |
| res. SMBV-Q | 21% | 20% | 20% | 20% |

Histological studies conducted in parallel showed that the observed fluorescence is not granular, and is generally visible at the apical pole of the cells.

Example V
Comparison of Intranasal Administration of a Monovalent Split of an Influenza Virus Antigen in Biovectors With Intranasal (i.n.) and Subcutaneous (s.c.) Administrations of HA Alone.

The antigen used in this study was a commercially available monovalent split of hemagglutinin (HA) and neuraminidase (N) prepared from viral membranes. The study was performed by administering 5 µg of the antigen in three groups of six BALB/c mice per group. Two groups received antigen alone, one group i.n. and the other group s.c. The third group received antigen in a dispersed, positively charged Biovector (SMBV-Q) that had an amphiphilic layer (DPPC/cholesterol in a ratio of 70:30) prepared in accordance with Example I(e). The antigen was injected subcutaneously (s.c.) or administered intranasally (i.n.) at day zero and day twenty one. The antibody response was analyzed at day thirty five by ELISA and by inhibitory hemagglutination against Nib16. The results are shown in Table V-1:

TABLE V-1

Response to administration i.n. of antigen

| Administration of Flu Vaccine | Total ELISA responses in sera | | | ELISA responses in nasal pharyngeal washings | |
|---|---|---|---|---|---|
| | IgG | IHA | IgA | Specific IgG | Specific IgA |
| subcutaneous | 350 000 | 320 | 0 | 64 | 0 |
| intranasal | 2 000 | 0 | 0 | 0 | 1,5 |
| intranasal in Disp. SMBV-Q | 145 000 | 240 | 581 | 48 | 128 |

Example VI
Comparison of Routes of Administration of gp160 of HIV With Biovectors.

Several successive immunizations at one month intervals were made in rabbits against the protein gp160 of HIV: two vaginal applications, two oral administrations and one intramuscular injection. Four female rabbits received five doses of 10 µg of gp160 of HIV, formulated in either:

(a) a solution containing the subunit B of the cholera toxin (CTB), the exotoxin of *Vibrio cholerae* which is a potent mucosal adjuvant.

(b) a solution of positively charged, dispersed light Biovectors (disp. SMBV-Q2). The solution contained 1.95 mg/ml of Biovector (1.5 mg/ml of polysaccharide core and 0.45 mg/ml of lipid, e.g., DPPC/cholesterol) per 100 µg/ml of gp160.

(c) a solution of lyophilized, positively charged light Biovectors resuspended in PBS (resuspended light Biovectors—res. SMBV-Q3). The solution contained 1.95 mg/ml of Biovector (1.5 mg/ml of polysaccharide core and 0.45 mg/ml of lipid, e.g., DPPC/cholesterol) per 100 µg/ml of gp160.

Immunizations were made as follows: vaginal at day $D_0$ and $D_{30}$, oral at day $D_{60}$ and $D_{90}$ and intramuscular at day $D_{120}$.

Ten days after each immunization (days $D_{40}$, $D_{70}$, $D_{100}$ and $D_{130}$), the specific IgAs in the vagina mucosa and in the saliva were measured by ELISA. The results are shown in the Table below.

TABLE VI-1

Vaginal administration of gp160 of HIV delivered by Biovectors

| | IgAs in vagina at $D_{40}$ | IgAs in saliva at $D_{40}$ |
|---|---|---|
| gp160-CTB | 0.41 | 0.42 |
| gp160-disp SMBV-Q | 0.42 | 0.42 |
| gp160-res. SMBV-Q | 0.65 | 0.60 |

TABLE VI-2

Oral Administration of gp160 of HIV delivered by Biovectors

| | IgAs in saliva | | IgAs in vagina |
|---|---|---|---|
| | $D_{70}$ | $D_{100}$ | $D_{100}$ |
| gp160-CTB | 0.42 | 0.38 | 0.28 |
| gp160-disp SMBV-Q | 0.47 | 0.35 | 0.29 |

Table VI-2 shows that, after the last vaginal administration, oral administration maintains the mucosal immunity at the same level.

Again, the Biovectors are as least efficient as CTB in maintaining specific IgA secretion by the vagina and the saliva.

TABLE VI-3

Intramuscular Administration of gp160 of HIV Delivered by Biovectors

| Day $D_{130}$ | IgAs in saliva | IgAs in vagina |
|---|---|---|
| gp160-CTB | 0.16 | 0.08 |
| gp160-disp SMBV-Q | 0.05 | 0.16 |

Table VI-3 shows that, at day $D_{130}$, the mucosal immunization does not persist. The intramuscular injection is not able to re-boost it.

The Biovector therefore appears to induce mucosal immunity when used to deliver antigens at the mucosal level. It is a vector of active compounds particularly adapted to mucosal administrations.

Example VII
Influenza Hemagglutinin Delivered Intranasally by Biovectors

Samples of four female mice were immunized at day $D_0$ and boosted at $D_{14}$ with 5 µg of hemagglutinin (HA) applied intranasally in 20 µl or 50 µl of a PBS solution or suspension, either alone or in a Biovector formulation. One group of animals was subjected to light ether anesthesia (*), while the others were awake. Administration of 20 µl on the outer nostrils of awake animals restricts the antigen to the upper respiratory tract. A volume of 50 µl directly into the nostrils of anesthetized animals results in deposition of at least part of the antigen in the lower respiratory tract and the lung, besides deposition in the nasal cavity.

Four different Biovectors were used: positively (SMBV-Q) and negatively (SMBV-P) charged light Biovectors, either resuspended (res) or dispersed (disp).

The influenza virus subunit antigen was either pre-loaded in the Biovectors (HA in SMBV) or simply post-loaded (HA+SMBV), i.e., admixed with them immediately before administration to the animals. The antigen alone was used as a control. The quality of the material used in the present study was equivalent to that for human vaccination purposes.

At day $D_{28}$, the mice were sacrificed. Serum samples were taken from the vena porta and antigen specific antibodies were measured in a direct enzyme-linked immunosorbent assay (ELISA). The results are shown in Table VII-1.

TABLE VII-1

Response to i.n. administration of HA in Biovectors. The numbers are serum IgG titers (geometric mean) determined as the reciprocal of the sample dilution that corresponds to an absorbance at 492 nm of 0.2 above background.

| Administration of HA | Unanesthetized animals | | | anesthetized animals | |
|---|---|---|---|---|---|
| | HA | HA in SMBV | HA + SMBV | HA | HA in SMBV |
| alone | 100 | | | 200 | |
| disp. SMBV-P | | 200 | 200 | | 60 |
| res. SMBV-P | | 400 | 30 | | 30 |
| res. SMBV-Q | | 10 | 20 | | 30 |
| disp. SMBV-Q | | 2000 | 2000 | | 4000 |

Example VIII
Intranasal Administration of Biovectors™ in Humans

VIII(a). Residence time of Biovectors™ in human nasal cavity

Ten fasted, healthy, male, non smoking subjects, having the age between 18 and 35 years were administered 1.5 mg of a $^{111}$I-radiolabelled formulation of SMBV-Q2 in each nostril (100 µl/nostril). This dose was equivalent to approximately 0.05 mg/kg in a 60 kg body. The study was a non-randomized three-way cross-over study.

Figure 3:
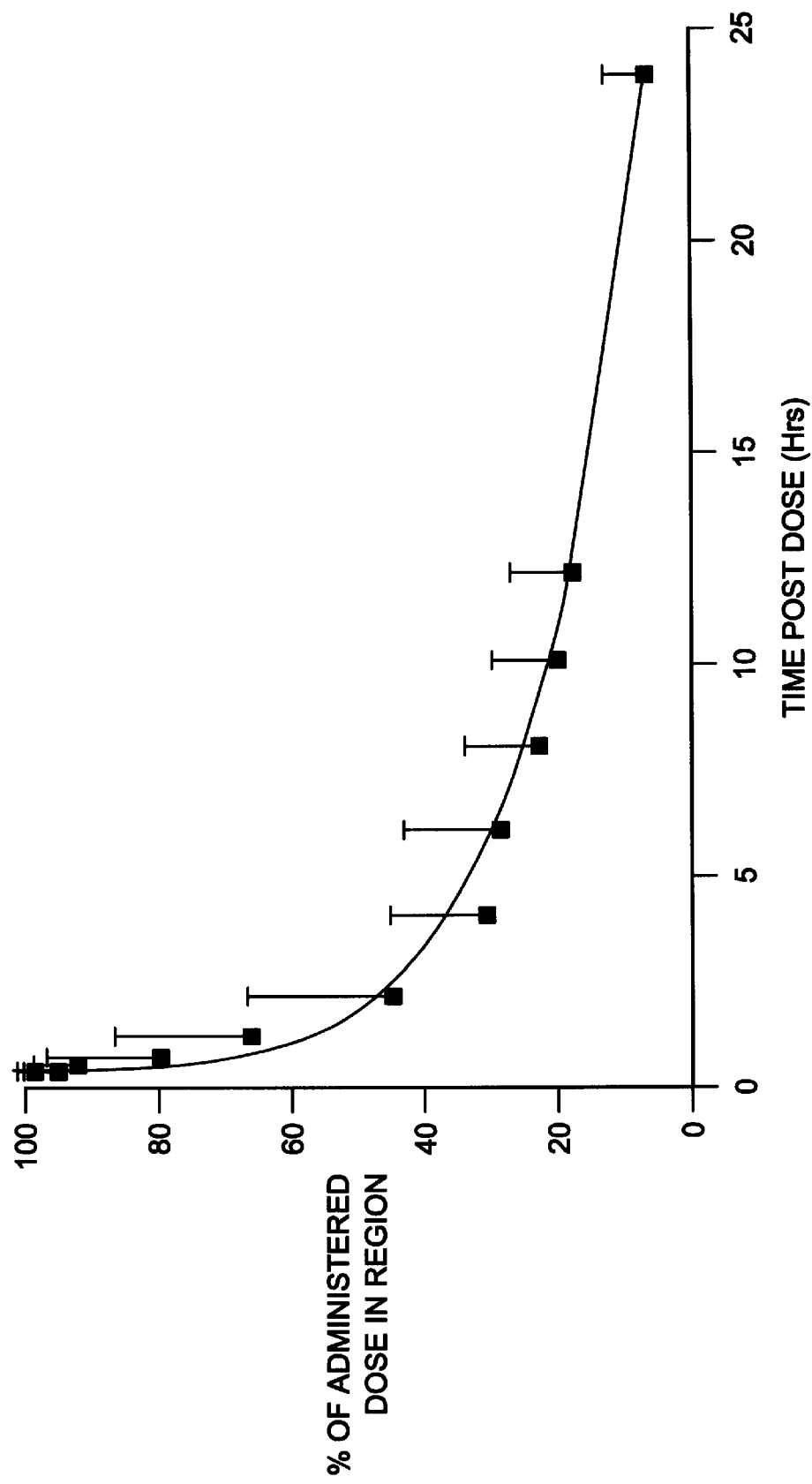
FIG. 3 shows the mean concentrations of radioactivity as a percentage of the administered dose in the nasal cavity of human volunteers.

Following intranasal administration, scintigraphic images were collected with a γ camera to ascertain the retention of the administered radioactivity by the nasal mucosa A continuous series of lateral head images were collected. The concentration of radioactivity in the nasal cavity showed a steady decline over the duration of the study. Twenty and seven percent of the dose was still detected at 12 and 24 hours, respectively, which is an extended period of retention for a solution, when compared to the prior art. The clearance time of one half the dose from the nasal cavity was approximately two hours, with a two compartment model. These results, which are shown in FIG. 3, confirm the potential of Biovectors™ for sustained delivery of materials to the nasal cavity.

VIII(b). Biodistribution of $^{111}$Indium-radiolabelled Biovector™ after administration to humans Following the administration of the radiolabelled formulations of Biovectors™ in the nose of the volunteers, in addition to the γ counts detected in the nasal region (as described above), counts were also detected in other regions of interest (e.g., lungs, stomach, small intestine/colon), which are expressed as a percentage of the maximum number of counts detected. This allowed the observed movement of radioactivity through the body to be quantified. Values were also determined for urinary and fecal radioactivity in total urine and fecal samples collected over 24 hours.

Figure 4:
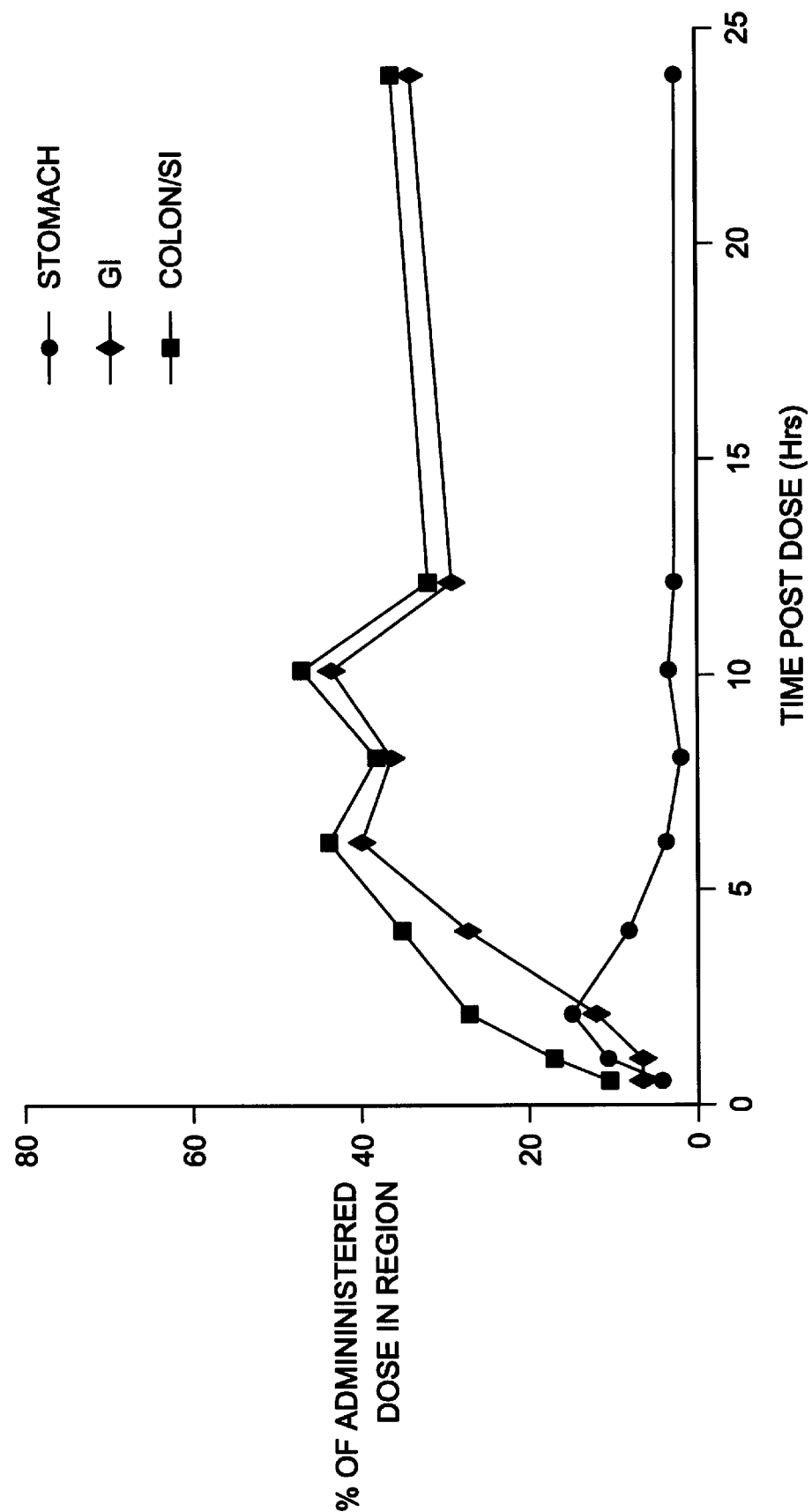
FIG. 4 shows the mean concentrations of radioactivity in the stomach and intestine cavities as a percentage of the administered dose versus time.

The nasal dosages cleared from the nasal cavity were usually swallowed, and subsequently excreted via the gastrointestinal tract. This elimination of the nasal dosages was supported by the fact that considerable amounts of radioactivity were detected in the stomach at early time points, and later in the small intestine/colon. A good inverse correlation could be made between the amount of radioactivity remaining in the small intestine/colon and the amount of radioactivity excreted in the feces. In the regions of interest examined, no significant radioactivity was detected that could be associated with any other identifiable tissue or organ. Very little radioactivity was detected in the urine indicating that only small quantities of the dose had been systemically absorbed. On the contrary, in many of the volunteers, a large amount of radioactivity was detected in the small intestine/colon at 24 hrs after dosing (mean ⅓ of the initial dose) indicating that this material had yet to be excreted. These results are shown in FIG. 4. Thus, the above results illustrate that the formulation of SMBV-Q2 is mucoadhesive and has significant potential for diagnostic purposes, e.g. of the gastro-intestinal tract (GI) region.

Example IX
Evaluation of Nasal Administration of Purified Hemagglutinin (Ha)/Biovector Formulations Influenza protein solution is based on split influenza vaccine, which is a blend of different influenza proteins: hemagglutinin (HA), neuraminidase (NA) and other viral proteins such as matrix protein, nucleoprotein and three polymerases. The hemagglutinin is considered to be the major antigen of this split. In order to characterize the binding of HA to SMBV, we analyzed the binding of purified HA to SMBV. Purified HA was obtained from the influenza virus, (strain B/Harbin), using the classical bromelin method described in Wiley et al., Ann. Res. Biochem. 56:365–394 (1987).

IX(a). Study of the binding of HA to SMBV

Figure 5:
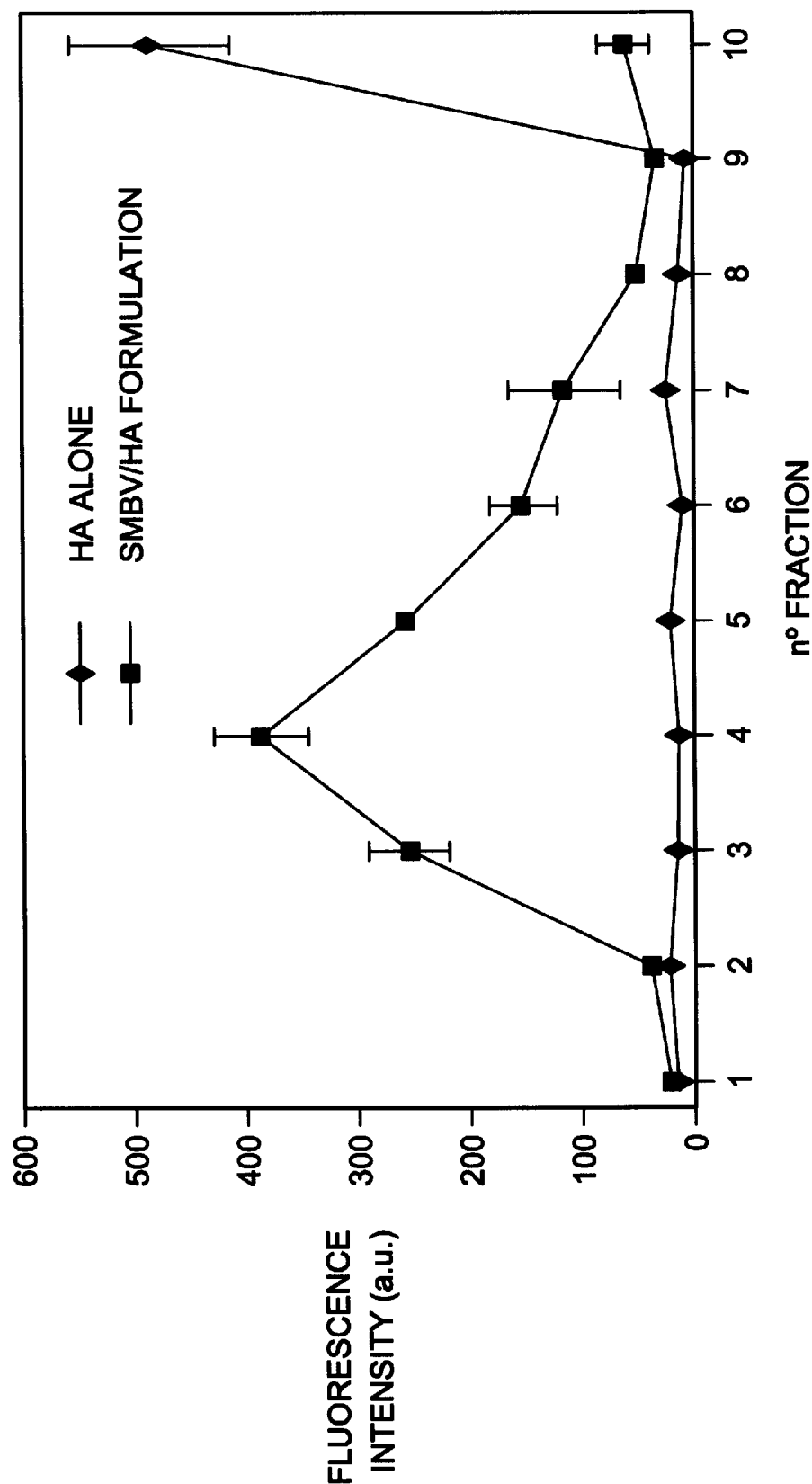
FIG. 5 shows sucrose gradient analysis (0 to 20%) of collected fractions for SMBV/HA formulation and HA alone, in which the protein was traced using protein intrinsic fluorescence at 280 nm or a protein assay (microBSA technique).
Figure 6:
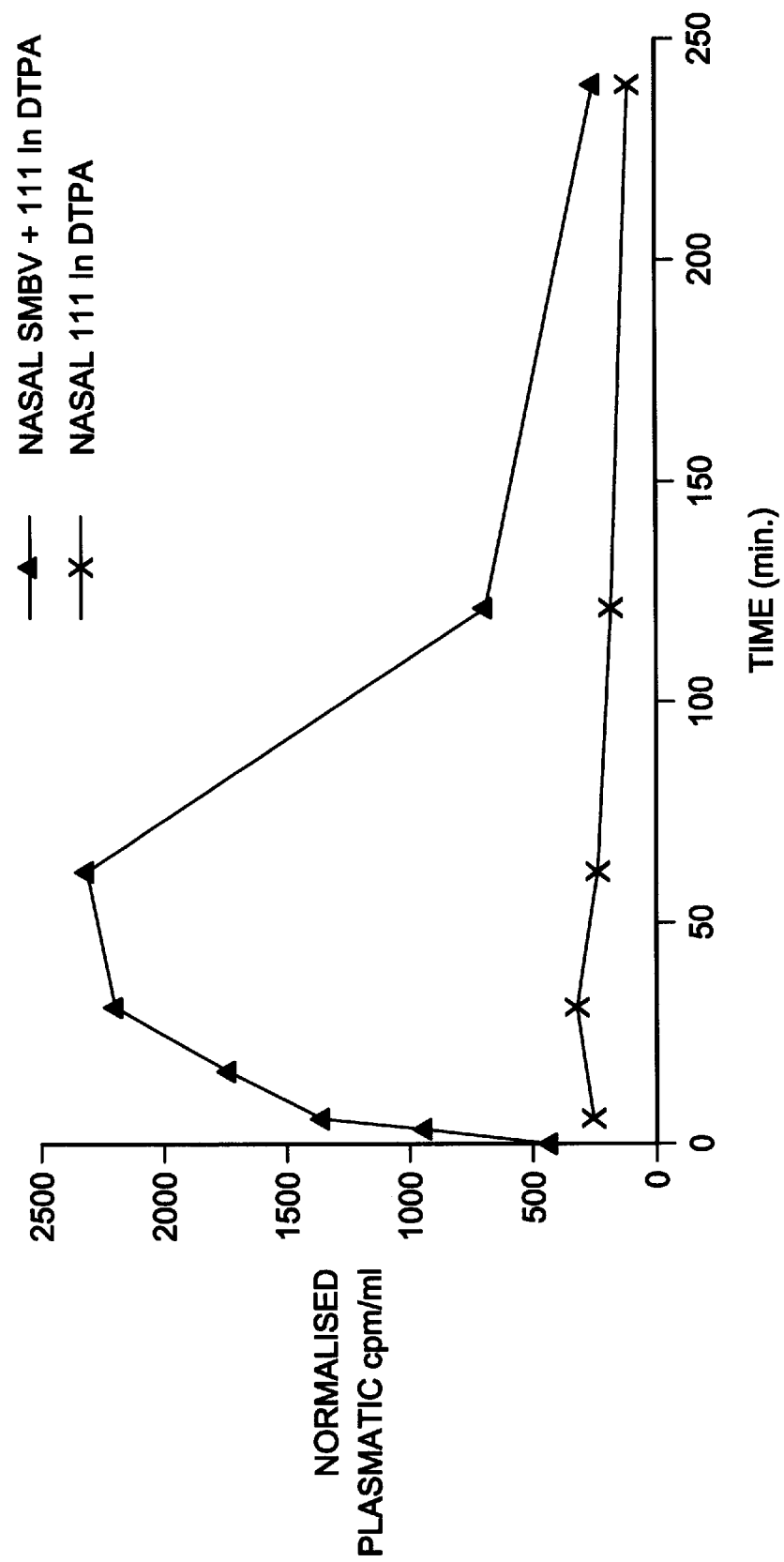
FIG. 6 shows normalized counts per minute/milliliter (cpm/ml) versus time for nasally administered $^{111}In$-DPTA+SMBV and $^{111}In$-DPTA.
Figure 7:
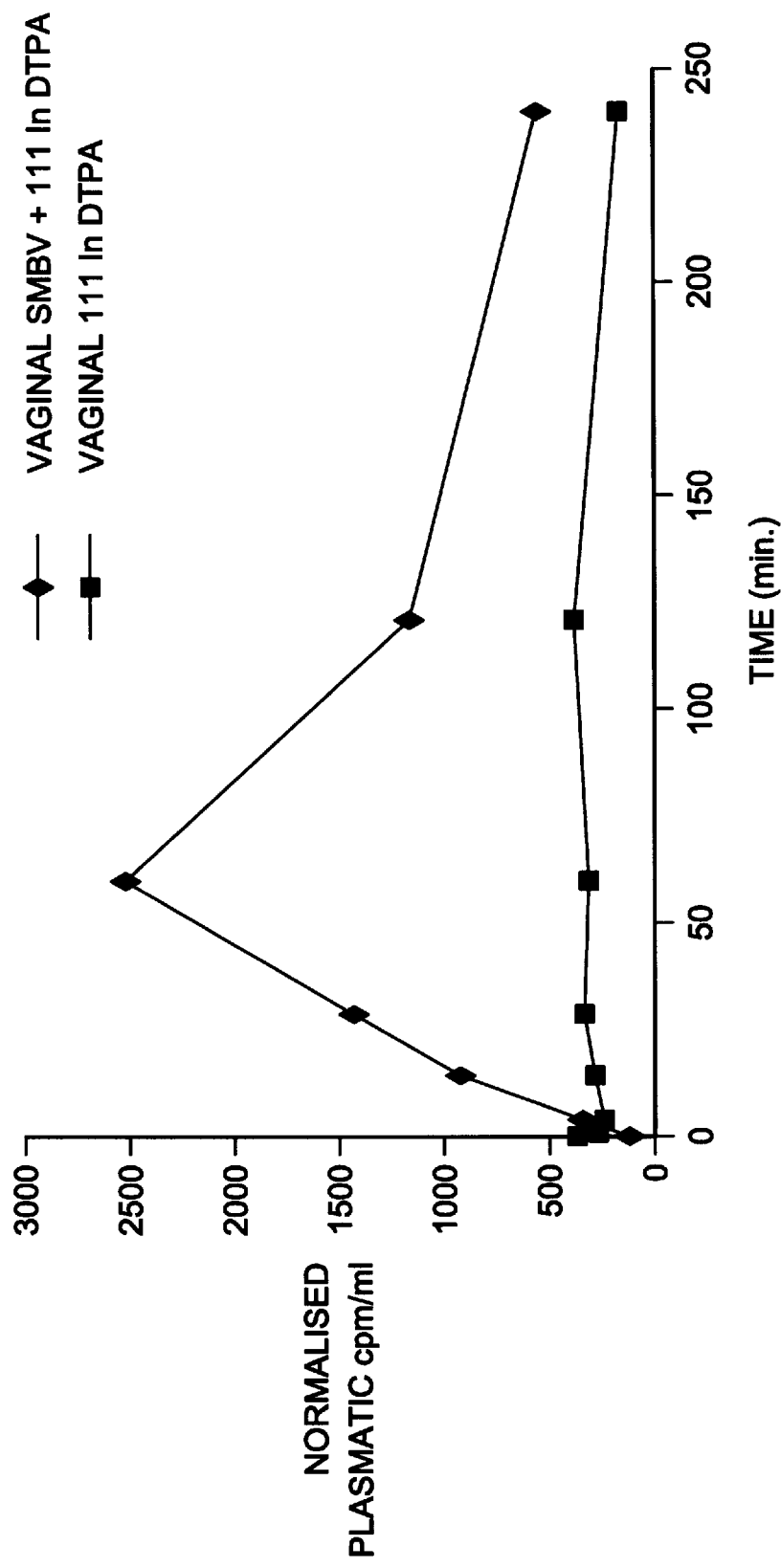
FIG. 7 shows normalized counts per minute/milliliter (cpm/ml) versus time for vaginally administered $^{111}In$-DPTA+SMBV and $^{111}In$-DPTA.
Figure 8:
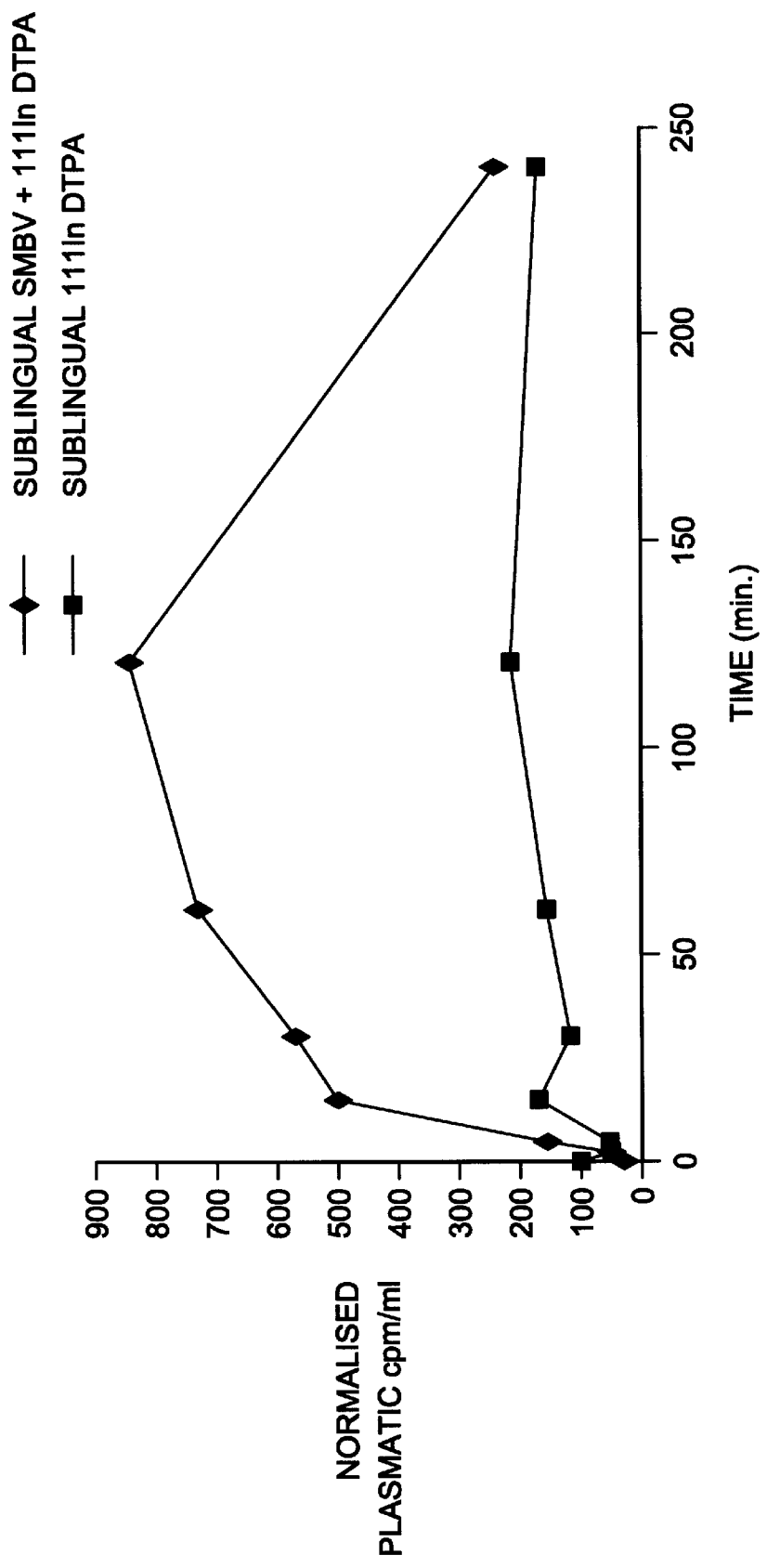
Figure 9:
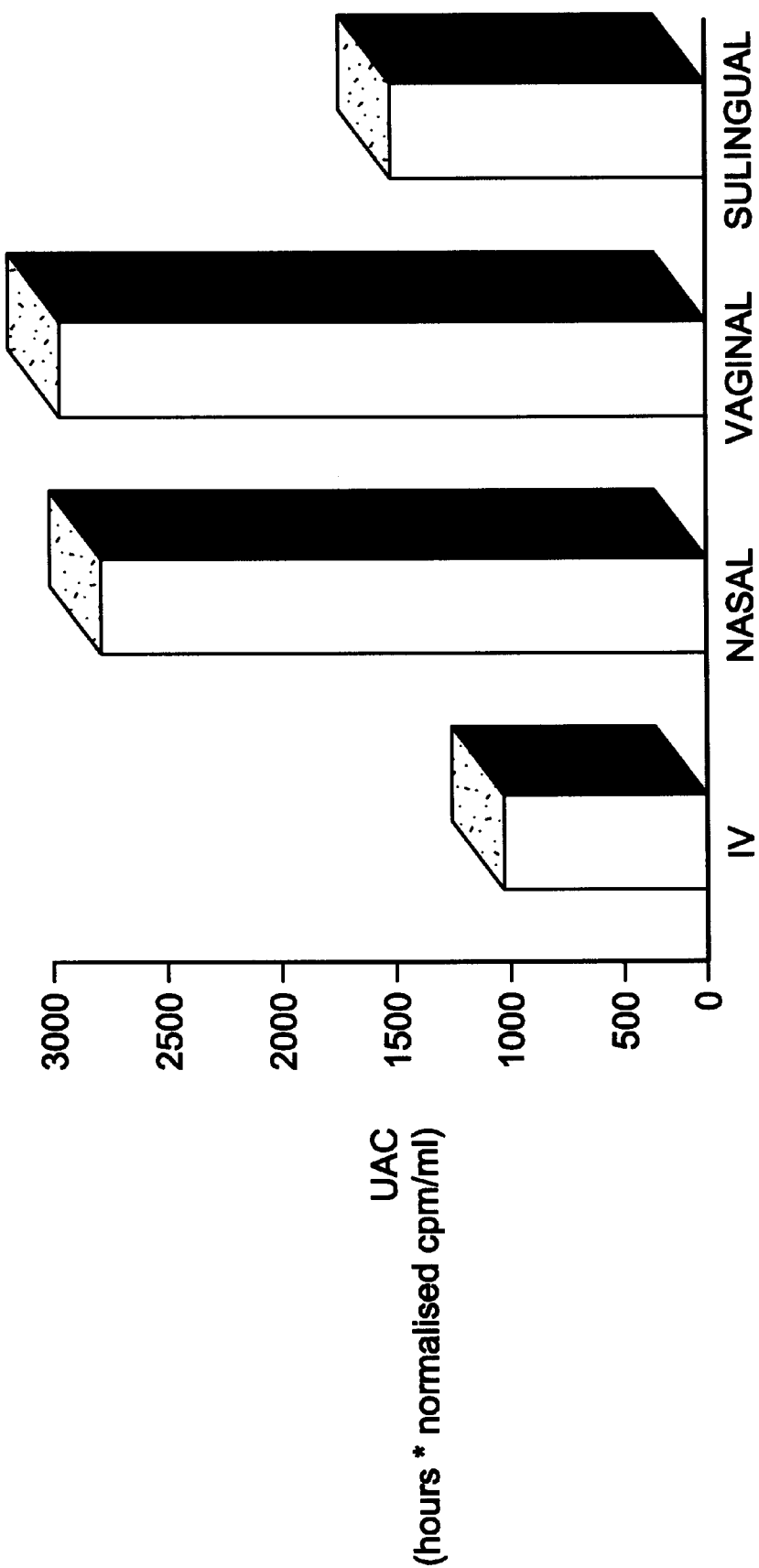

The yield of HA binding to SMBV was analyzed after separation of the formulations on sucrose gradient (0 to 20%). The sucrose gradient was used to separate free HA from HA bound to SMBV. Free HA was isolated to the last fraction of the gradient. Moreover, because HA was formulated with SMBV, a change in the density of the protein was observed due to its binding to SMBV. A nearly quantitative binding of HA to SMBV was observed. Protein content was assayed using microBCA technique or intrinsic fluorescence of antigens after irradiation at 280 nm (no difference was found using these two techniques). The result of this experiment are shown in FIG. 5.

IX(b) Response of mice to i.n. administration of HA in Biovectors™

Four female mice were immunized at day $D_0$ and boosted at day $D_{14}$ with 5 µg of hemagglutinin (HA) applied intranasally in 20 µl or 50 µ of a PBS solution or suspension, either alone or in a Biovector formulation. For 5 µg of HA, the HA/lipid ratio was ¹⁄₁₀, with the quantity of SMBV introduced being about 220 µg. One group of animals was subjected to light ether anesthesia. Administration of 20 µl on the outer nostrils of awake animals restricted the antigen to the upper respiratory tract. A volume of 50 μl was directly administered into the nostrils of anesthetized animals resulting in deposition of at least part of the antigen in the lower respiratory tract and the lung.

Figure 11:
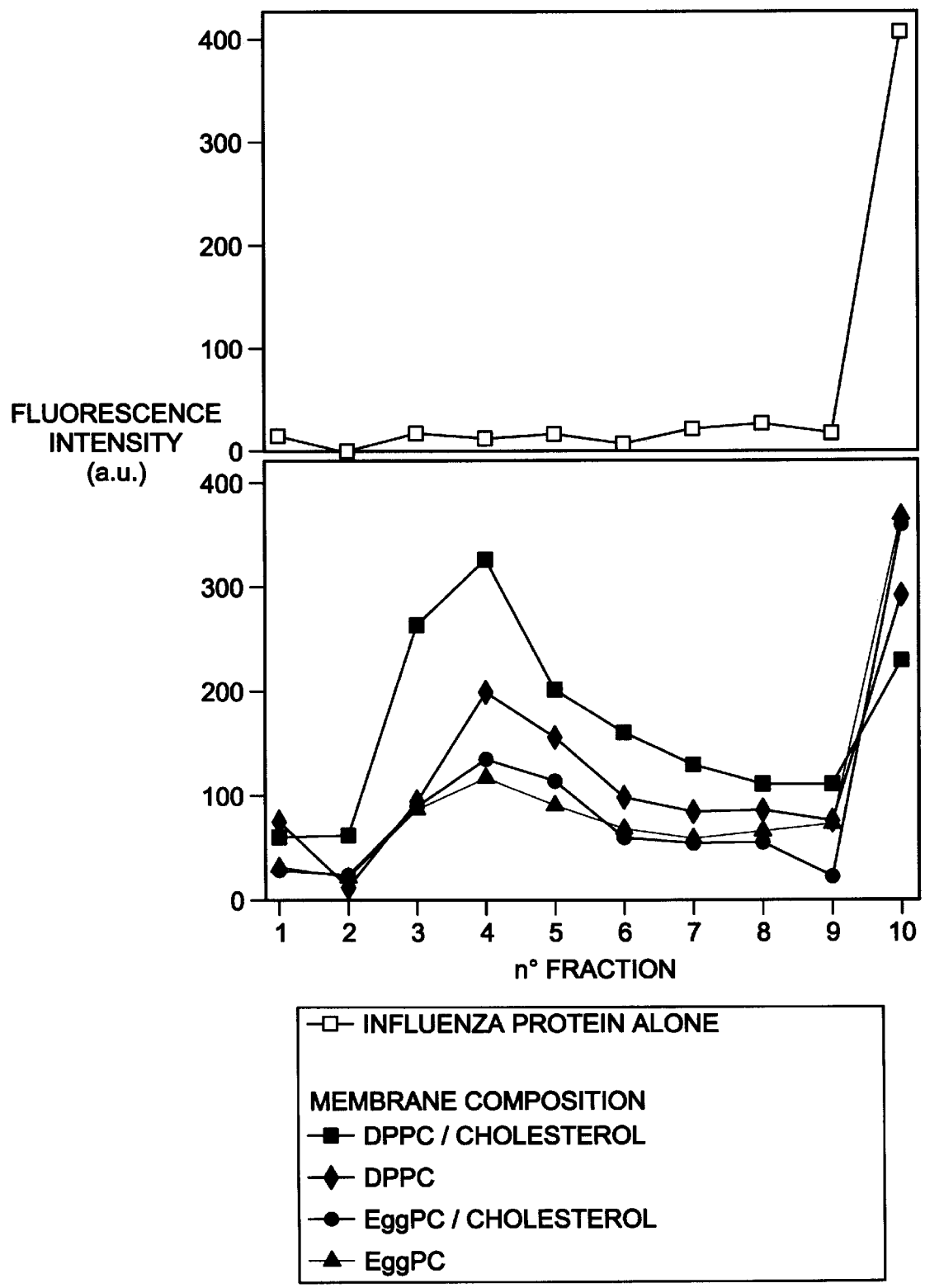

Four different biovectors were used: positively (SMBV-Q2, Q3) and negatively (SMBV-P2, P3) charged light biovectors, either resuspended (res.) or dispersed (disp.). The HA was either pre-loaded in the biovectors (HA in SMBV) or simply post-loaded (HA+SMBV), i.e., mixed before administration to the animals. The HA alone was used as a control. At day $D_{28}$, the mice were sacrificed. Serum samples were taken and antigen specific antibodies were measured (ELISA). The results are shown below in the Table IX-1.

TABLE IX-1

Response to i.n. administration of HA in Biovectors. The number are serum IgG titers (geometric mean) determined as the reciprocal of the sample dilution that corresponds to an absorbance at 492 nm of 0.2 background.

| | Unanesthetized Animals | | | Anesthetized Animals | |
|---|---|---|---|---|---|
| Administration of HA | HA | HA in SMBV | HA + SMBV | HA | HA in SMBV |
| Alone | 100 | | | 200 | |
| Disp. SMBV-P2 | | 200 | 200 | | 60 |
| Res. SMBV-P3 | | 400 | 30 | | 30 |
| Res. SMBV-Q3 | | 10 | 20 | | 30 |
| Disp. SMBV-Q2 | | 2000 | 2000 | | 4000 |

Example X

Nasal, Vaginal and Sublingual Administration of Diethylenetriamine Pentaacetic Acid (DTPA)

DTPA was used as a diagnosis tool, allowing administration of compounds such as indium, and gadolinium. DTPA is hydrophilic and considered to be an efficient marker of extracellular water, rapidly cleared from plasma (H. J Weinmenn, R C et al, Characteristic of Gd-DTPA—a potential NMR constrast agent, A.J.R. 142:619 (1984); Brasch R. C. et al., Constrast enhanced NMR imaging. Animal study using gadolinium DTPA complex., A.J.R 142:625 (1984); Doucet D. et al. in enhanced magnetic resonance imaging, p87–92. Editor val M. Runge and C. V. Mosby. Company edition (St Louis, Mo.) (1989)).

The cationic SMBV was loaded with $^{111}$In-DTPA. For this purpose, one volume of DTPA (Fluka) solution (12 mM in water) was labeled with one volume of $^{111}InCl_3$ (10 mCi/ml Cisbio). One volume of cationic SMBV, as prepared in example I(e)(SMBV-Q2), with charge density of 2 mEq/g, at 20 mg/ml in water, was mixed with one volume of $^{111}$In-DTPA solution (6 mM). A control preparation was also prepared following the same procedure but without cationic SMBV.

Both preparations were administered to female rats by three different mucosal routes: nasal, vaginal or sublingual. Following administration, at D+2 min., D+5 min., D+15 min., D+30 min., D+1 h., D+2 h. and D+4 h.(D being time zero), a small quantity of blood was taken from each animal and the radioactivity was measured with a gamma counter.

In addition, two controls were also performed. The first control was administration of the preparation by intravenous route. In this case, $^{111}$In-DTPA-SMBV-Q2 was diluted in citrate NaCl buffer (Sodium citrate 1 mM, NaCl 150 mM) in order to compensate for the low osmolarity of the preparation and because citrate buffer can inhibit molecular interaction between polycarboxylic compound like DTPA and cationic SMBV. The second control was performed by intranasal administration of the preparation diluted in a citrate buffer (1 mM, pH 6).

The results obtained after mucosal administration of $^{111}$In-DTPA-SMBV are shown in FIGS. 6, 7 and 8. These comparative pharmacokinetic studies show that nasal and vaginal routes of administration are comparable as to their $^{111}$In-DTPA absorption kinetics. The $^{111}$In-DTPA associated with cationic SMBV administered intranasally or intravaginally was rapidly absorbed, with an absorption half life of 7 min. and 27 min., respectively. The high rate of absorption is reflected by the time necessary to reach the peak plasma concentration ($T_{max}$). The $T_{max}$ was 30 min for intranasal route and 60 min for the vaginal route. After intranasal and vaginal administrations of $^{111}$In-DTPA-SMBV, the elimination half life of $^{111}$In-DTPA was 2.0 hours and 2.3 hours, respectively (compared to an elimination half life of 13 min after intravenous administration of $^{111}$In-DTPA-SMBV). This value can also be compared to the half life time of cationic SMBV after nasal administration in humans (2.3 hours, see example VIII).

Although, the result of sublingual administration of $^{111}$In-DTPA-SMBV seemed lower, a clear $^{111}$In-DTPA adsorption was also obtained by this route of administration.

Moreover, when $^{111}$In-DTPA-SMBV was administered intranasally in citrate buffer practically no adsorption was obtained. This result illustrated that the association between $^{111}$In-DTPA and cationic SMBV is necessary to obtain mucosal adsorption of $^{111}$In-DTPA.

Compared to intravenous administration (I.V.), all mucosal routes facilitated an increase of the plasmatic AUC (area under curve), which is representative of the residence time of $^{111}$In-DTPA in the plasma (see FIG. 9). In fact, intranasal or vaginal administration exhibited a 300% improvement over intravenous administration, while sublingual administration exhibited a 150% improvement.

Example XI

Comparison of Intranasal Administration of a Monovalent Split of an Influenza Virus Antigen in Biovectors with Intranasal and Subcutaneous Administration of Influenza Virus Antigen in Without Biovector XI(a). Study of the binding of the antigen to SMBV A split influenza vaccine was prepared from a blend of different influenza proteins: hemagglutinin (HA), neuraminidase (NA) and other viral proteins such as matrix protein, nucleoprotein and three polymerases. The hemagglutinin is considered to be the major antigen of this split. The binding of total split proteins to SMBV was analyzed using the same technique described in Example IX.

In order to ascertain whether or not the supramolecular structure of SMBV (binding of lipids to polysaccharide core) remained unchanged, different parts of SMBV were labeled. Inner part of SMBV-Q2 (PSC) was labeled with covalently bound fluorescein and the membrane with diphenylhexatriene (DPH). Total proteins were traced on a sucrose gradient (0 to 20%) using either a protein assay (microBCA technique) or fluorescence at 280 nm. The analysis of the collected fractions is shown FIG. 10.

From FIG. 10, one can observe that antigens were found in the same fractions as SMBV-Q2 (PSC+lipids), in which most of HA was bound to SMBV. Moreover, the supramolecular structure of SMBV (binding of PSC+lipids) remained unchanged when associated with antigens in the formulation.

In order to optimize split influenza protein binding to SMBV-Q2, different components for the outer layer were investigated (i.e. DPPC, DPPC/Cholesterol, egg-PC and egg-PC/Cholesterol). The controls were the inner PSC core alone (SMBV-Q1) and the outer layer component alone (i.e., as the membrane of a liposome), in which neither the outer layer component nor the PSC were labeled with a fluorescent agent to avoid any interference. The results are shown in FIG. 11, with the quantification analysis listed in Table XI-1.

TABLE XI-1

Analysis of the rate of association of split influenza antigens to nanoparticles. SMBV (PSC + lipids), or the components of SMBV: PSC or lipids (liposomes).

| Types of nanoparticles | Binding yield (%) |
|---|---|
| Liposomes | |
| Egg PC | nd |
| EggPC/Cholesterol (70/30, w/w) | nd |
| DPPC | 35 |
| DPPC/Cholesterol (70/30, w/w) | 11 |
| Polysaccharidic cores (PSC) (SMBV-Q1) | 37 |
| SMBV (SMBV-Q2) | |
| PSC/EggPC | 36 |
| PSC/EggPC/Cholesterol | 37 |
| PSC/DPPC | 52 |
| PSC/DPPC/Cholesterol | 90 |

As listed in Table XI-1, the binding of the influenzas antigens to liposomes, and to the polysaccharide core of SMBV-Q1 (PSC), were found to lie between 11 to 37%. However, the binding of the antigens to SMBV-Q2 (PSC/lipid complex) were found to be significantly higher, from 52% to 90%, depending on the membrane composition. This result can be explained by the SMBV supramolecular structure, with its dual properties. Antigens in this structure are bound to the outer layer and also stabilized by the cationic polysaccharide core underneath, with the best outer layer combination being DPPC/Cholesterol.

XI(b). Response of mice to intranasal administration of Influenza virus antigen in Biovectors as compared to intranasal and subcutaneous administration of the antigen alone A study was conducted to ascertain immunobioequivalent dosages of influenza antigens combined with Biovectors adminstered nasally (Flu/BV) and subcutaneous administration of free influenza antigens (Flu/Ag). The antigenic response induced by Flu/BV administered intranasally was compared to the antigenic response induced by subcutaneous administration of free Flu/Ag.

Nasal formulations were made by mixing influenza protein solutions, split influenza virus (Strain A/Singapore NIB16 H1N1), with a cationic SMBV suspension. Mice vaccinated with different Flu/BV formulations made of split influenza virus antigen (Flu/Ag) associated with SMBV-Q2 were evaluated.

Fifteen female mice BALB/cJ/Rj (10 weeks old) were divided into three groups (5 mice/group) and received either free Flu/Ag (control groups) or Flu/BV. The administration was performed on unanesthetized animals. A summary of the dosing protocol is listed in Table XI-2.

TABLE XI-2

| Antigen formulation | Route of administration: Priming | Boost | Volume (μl/administ.) | Lipid Quantity (μg/administ.) | HA Quantity (μg/administ.) |
|---|---|---|---|---|---|
| Free Flu/Ag | s.c. | s.c. | 100 | / | 5 |
| Free Flu/Ag | i.n. | i.n. | 25 | / | 5 |
| Flu/BV | i.n. | i.n. | 25 | 50 | 5 |

Description of the study for evaluation of the immunological response of split flu virus formulation. (s.c.: subcutaneous; i.n.: intranasal)

Mice were primed at $D_0$ and boosted at $D_{21}$, the analysis of the immune response was analyzed at $D_{35}$. Serums were sampled and antibody titers and Inhibitory Haemaglutination Assays (IHA) were analyzed. Nasal secretions were also obtained by washing the nasal cavities with 500 μl of Phosphate Buffered Saline, the level of nasal IgG and sIgA titers was then determined. The results of this analysis is listed in Table XI-3.

TABLE XI-3

| Antigen formulation | Administration | Seric response: Total IgG | IHA | Total sIgA | Nasal response: Specific IgG | Specific sIgA |
|---|---|---|---|---|---|---|
| Free Flu/Ag | S.C./S.C. | 350,000 | 320 | 00 | 64 | 0 |
| Free Flu/Ag | i.n./i.n. | 2,000 | 0 | 0 | 0 | 1.5 |
| Flu/BV | i.n./i.n. | 145,000 | 240 | 581 | 48 | 128 |

Immunological comparison of nasal administration of Flu/BV formulation versus free Flu/Ag administered either intranasally or subcutaneously. The mice were primed at $D_0$, boosted at $D_{21}$ and immunological response was analyzed at $D_{35}$. For each group the dose of HA was 5 μg.

Free Flu/Ag administered subcutaneously induced a strong seric IgG response associated with high IHA titers. When compared to the subcutaneous control, free antigen intranasally administered failed to induce any specific seric response. In contrast, nasal Flu/BV formulation induced a strong seric response similar to that obtained with free antigen subcutaneously administered. In addition, nasal administration of the Flu/BV formulation elicited specific sIgA in nasal washings. In contrast, free Flu/Ag administered either intranasally or subcutaneously failed to induce any mucosal response.

Apparent from the above results, the intranasal Influenza antigen associated with cationic SMBV (Flu/BV Formulation) was able to induce both IgG and IHA titers equivalent to the subcutaneous administration of free Flu/Ag. Moreover, only the Flu/BV formulation administered intranasally induced high IgA titers in serum and importantly nasal sIgA antibody responses.

We claim:

1. A method for the mucosal administration of a substance to a mammal, the method comprising contacting a mucosal surface of the mammal with the substance in combination with a Biovector core, wherein the Biovector core comprises a natural polymer or a hydrolysate of a natural polymer, or a mixture thereof, and wherein the core is uncoated; or is partially or completely coated with no more than one layer, the layer comprising a lipid compound covalently bonded to the core, or an amphiphilic compound.

2. The method of claim 1, wherein the natural polymer is selected from the group consisting of a cross-linked polysaccharide, a cross-linked oligosaccharide, or hydrolysate of a cross-linked polysaccharide or a cross-linked oligosaccharide, and a mixture thereof.

3. The method of claim 2, wherein the cross-linked polysaccharide and cross-linked oligosaccharide are selected from the group consisting of starch, dextran, dextrin, and maltodextrin.

4. The method of claim 2, wherein 0 to 2 milliequivalents of ionic charge per gram is grafted to the cross-linked polysaccharide or cross-linked oligosaccharide.

5. The method of claim 4, wherein the ionic charge is a positive charge.

6. The method of claim 5, wherein the positive charge is due to the presence of a cationic or basic group selected from the group consisting of a quaternary ammonium group, a primary amine, a secondary amine, and a tertiary amine.

7. The method of claim 5, wherein the positive charge is due to the presence of a quaternary ammonium group.

8. The method of claim 5, wherein the positive charge is due to the presence of a ligand selected from the group consisting of choline, 2-hydroxypropyltrimethylammonium, 2-dimethylaminoethanol, 2-diethylaminoethanol, 2-dimethylaminoethylamine, and 2-diethylaminoethylamine and an amino acid.

9. The method of claim 4, wherein the ionic charge is a negative charge.

10. The method of claim 9, wherein the negative charge is due to the presence of a an anionic or acidic group selected from phosphate, a sulfate, and carboxylate.

11. The method of claim 9, wherein the negative charge is due to the presence of a phosphate group.

12. The method of claim 2, wherein the cross-linked polysaccharide or cross-inked oligosaccharide is coated partially or completely with a layer of an amphiphilic compound.

13. The method of claim 12 wherein the amphiphilic compound is a phospholipid or a ceramide.

14. The method of claim 13 wherein the phospholipid is selected from the group consisting of phosphatidyl choline, phosphatidyl hydroxycholine, phosphatidyl ethanolamine, phosphatidyl serine, and phosphatidyl glycerol.

15. The method of claim 1, wherein the diameter of the Biovector is 20–200 mn.

16. The method of claim 1, wherein the diameter of the Biovector is 20–100 nm.

17. The method of claim 1, wherein the cross-linked polysaccharide or cross-linked oligosaccharide binds non-specifically to the mucosal surface.

18. The method of claim 1, wherein the Biovector is dispersed.

19. The method of claim 1, wherein the Biovector is dried.

20. The method of claim 19, wherein the dried Biovector is resuspended.

21. The method of claim 1, wherein the substance is a therapeutic agent, a prophylactic agent, or a diagnostic agent.

22. The method of claim 21, wherein the therapeutic agent is selected from the group consisting of a radiopharmaceutical, an analgesic drug, an anesthetic agent, an anorectic agent, an anti-anemia agent, an anti-asthma agent, an anti-diabetic agent, an antihistamine, an anti-inflammatory drug, an antibiotic drug, an antimuscarinic agent, an anti-neoplastic drug, an antiviral drug, a cardiovascular drug, a central nervous system stimulant, a central nervous system depressant, an anti-depressant, an anti-epileptic, an anxyolitic agent, a hypnotic agent, a sedative, an anti-psychotic drug, a beta blocker, a hemostatic agent, a hormone, a vasodilator, a vasoconstrictor, and a vitamin.

23. The method of claim 21, wherein the prophylactic agent is a vaccine against a pathogen.

24. The method of claim 1, wherein the pathogen is selected from the group consisting of a virus, a bacterium, a yeast, and a fungus.

25. The method of claim 24, wherein the virus is selected from the group consisting of an influenza virus, a cytomegalovirus, HIV, a papilloma virus, a respiratory syncytial virus, a poliomyelitis virus, a pox virus, a measles virus, an arbor virus, a Coxsackie virus, a herpes virus, a hantavirus, a hepatitis virus, a lyme disease virus, a mumps virus, and a rotavirus.

26. The method of claim 25, wherein the virus is an influenza virus.

27. The method of claim 25, wherein the virus is HIV.

28. The method of claim 24, wherein the bacterium is selected from the group consisting of a member of the genus Neisseria, Aerobacter, Pseudomonas, Porphyromonas, Salmonella, Escherichia, Pasteurella, Shigella, Bacillus, Helibacter, Corynebacterium, Clostridium, Mycobacterium, Yersinia, Staphylococcus; Bordetella, Brucella, Vibrio, and Streptococcus.

29. The method of claim 24, wherein the pathogen is a member of a genus selected from the group consisting of Plasmodium, Schisostoma, and Candida.

30. The method of claim 21, wherein the diagnostic agent is a contrast agent or an imaging agent.

31. The method of claim 21, wherein the diagnostic agent detects corneal irregularities.

32. The method of claim 21, wherein the diagnostic agent is labeled with a detectable group.

33. The method of claim 32, wherein the detectable group is selected from the group consisting of a radioactive group, a magnetic group, and a fluorescent group.

34. The method of claim 1, wherein the substance is a small chemical molecule.

35. The method of claim 34, wherein the small chemical molecule is selected from the group consisting of an organic molecule, an inorganic molecule, and an organo-metallic molecule.

36. The method of claim 1, wherein the substance is a biological molecule.

37. The method of claim 36, wherein the biological molecule is selected from the group consisting of an amino acid, an oligopeptide, a peptide, a protein, a glycoprotein, a lipoprotein, a proteoglycan, a lipopolysaccharide, a fatty acid, an eicosanoid, a lipid, a triglyceride, a phospholipid, a glycolipid, a nucleoside, a nucleotide, a nucleic acid, a DNA molecule, an RNA molecule, a monosaccharide, an oligosaccharide, and a polysaccharide.

38. The method of claim 1, wherein more than one substance is administered in combination with the Biovector.

39. The method of claim 2, wherein the substance is located in the inner core of the cross-linked polysaccharide or cross-linked oligosaccharide.

40. The method of claim 2, wherein the substance is located at the outer surface of the cross-linked polysaccharide or cross-linked oligosaccharide.

41. The method of claim 12, wherein the substance is located in the inner core of the amphiphilic compound layer.

42. The method of claim 12, wherein the substance is located at the outer surface of the layer.

43. The method of claim 1, wherein the substance is added to the Biovector prior to administration to the mammal.

44. The method of claim 1, wherein the substance and the Biovector are mixed together at the time of administration to the mammal.

45. The method of claim 1, wherein the mucosal surface is selected from the group consisting of a nasal, buccal, oral, vaginal, ocular, auditory, pulmonary tract, urethral, digestive tract, and rectal surface.

46. The method of claim 45, wherein the mucosal surface is selected from the group consisting of a nasal, vaginal, and ocular surface.

47. The method of claim 1, wherein the natural polymer is grafted with ionic ligands.

48. The method of claim 2, wherein the cross-linked polysaccharide or oligosaccharide is grafted with ionic ligands.

* * * * *

UNITED STATES PATENT AND TRADEMARK OFFICE
CERTIFICATE OF CORRECTION

PATENT NO. : 6,017,513
DATED : January 25, 2000
INVENTOR(S) : Betbeder et al.

It is certified that error appears in the above-identified patent and that said Letters Patent is hereby corrected as shown below:

<u>Claim 24,</u>
Delete "claim 1, wherein" and insert therefor -- claim 23, wherein --.

Signed and Sealed this

Twenty-fifth Day of December, 2001

*Attest:*

JAMES E. ROGAN
*Attesting Officer*     *Director of the United States Patent and Trademark Office*